US010582891B2

(12) United States Patent
Wiedenhoefer et al.

(10) Patent No.: US 10,582,891 B2
(45) Date of Patent: Mar. 10, 2020

(54) SYSTEM AND METHODS FOR MONITORING PHYSICAL THERAPY AND REHABILITATION OF JOINTS

(71) Applicant: Consensus Orthopedics, Inc., El Dorado Hills, CA (US)

(72) Inventors: Curt Wiedenhoefer, Davis, CA (US); Justin Anthony Creel, Fair Oaks, CA (US); Brian James Katerberg, Folsom, CA (US); Joshua Dale Howard, Sacramento, CA (US)

(73) Assignee: CONSENSUS ORTHOPEDICS, INC., El Dorado Hills, CA (US)

( * ) Notice: Subject to any disclaimer, the term of this patent is extended or adjusted under 35 U.S.C. 154(b) by 0 days.

(21) Appl. No.: 15/422,299

(22) Filed: Feb. 1, 2017

(65) Prior Publication Data
US 2017/0143261 A1  May 25, 2017

Related U.S. Application Data

(63) Continuation-in-part of application No. 15/077,809, filed on Mar. 22, 2016.
(Continued)

(51) Int. Cl.
*A61B 5/05* (2006.01)
*A61B 5/00* (2006.01)
(Continued)

(52) U.S. Cl.
CPC ............ *A61B 5/4851* (2013.01); *A61B 1/041* (2013.01); *A61B 5/002* (2013.01); *A61B 5/0013* (2013.01);
(Continued)

(58) Field of Classification Search
CPC ............ A61B 5/11; A61B 5/45; A61B 5/4528; A61B 5/4851
See application file for complete search history.

(56) References Cited

U.S. PATENT DOCUMENTS 3,724,651 A    4/1973   Link
4,353,135 A    10/1982  Forte et al.
(Continued)

FOREIGN PATENT DOCUMENTS

EP    1938749       7/2008
WO    2008/120215   10/2008
(Continued)

OTHER PUBLICATIONS

International Search Report and Written Opinion for PCT/US2016/023637 dated Aug. 9, 2016.
(Continued)

*Primary Examiner* — Michael J D Abreu
(74) *Attorney, Agent, or Firm* — Lowe Graham Jones PLLC; Bruce E. Black

(57) ABSTRACT

A system for monitoring a patient includes a sensor unit having a housing and sensors disposed in or around the housing; and a base having a shell and configured and arranged to be adhesively attached to skin of the patient. The sensors can be used to monitor physical therapy and rehabilitation of the patient. The sensor unit can provide information to a patient or clinician device to facilitate the monitoring. The sensor data can be used to determine measurements such as tilt angle of the sensor unit and range of motion measurements (such as extension, flexion, or forces associated with movement) of the anatomical region to which the sensor unit is attached. The sensor data can also be used for automated identification or classification of exercises performed by the patient.

20 Claims, 14 Drawing Sheets

Related U.S. Application Data

(60) Provisional application No. 62/136,925, filed on Mar. 23, 2015, provisional application No. 62/136,892, filed on Mar. 23, 2015.

(51) Int. Cl.

| | | |
|---|---|---|
| A61B 5/11 | (2006.01) | |
| A61B 5/107 | (2006.01) | |
| A61B 5/01 | (2006.01) | |
| A61B 5/024 | (2006.01) | |
| A61B 5/07 | (2006.01) | |
| A61B 1/04 | (2006.01) | |
| G01C 22/00 | (2006.01) | |
| A61B 90/30 | (2016.01) | |

(52) U.S. Cl.
CPC .......... *A61B 5/0015* (2013.01); *A61B 5/0022* (2013.01); *A61B 5/0031* (2013.01); *A61B 5/0035* (2013.01); *A61B 5/0086* (2013.01); *A61B 5/01* (2013.01); *A61B 5/024* (2013.01); *A61B 5/076* (2013.01); *A61B 5/1071* (2013.01); *A61B 5/112* (2013.01); *A61B 5/1121* (2013.01); *A61B 5/1126* (2013.01); *A61B 5/4528* (2013.01); *A61B 5/4585* (2013.01); *A61B 5/4848* (2013.01); *A61B 5/686* (2013.01); *A61B 5/6833* (2013.01); *A61B 5/6878* (2013.01); *A61B 5/742* (2013.01); *G01C 22/006* (2013.01); *A61B 2090/309* (2016.02); *A61B 2505/09* (2013.01); *A61B 2560/0214* (2013.01); *A61B 2562/0219* (2013.01); *A61B 2562/0223* (2013.01); *A61B 2562/0247* (2013.01)

(56) References Cited

U.S. PATENT DOCUMENTS

| | | | |
|---|---|---|---|
| 4,756,312 | A | 7/1988 | Epley |
| 5,833,603 | A | 11/1998 | Kovacs et al. |
| 6,588,931 | B2 | 7/2003 | Betzner et al. |
| 2003/0069714 | A1 | 4/2003 | Wigley et al. |
| 2003/0163287 | A1 | 8/2003 | Vock et al. |
| 2004/0122334 | A1 | 6/2004 | Yamashiro |
| 2004/0167390 | A1 | 8/2004 | Alexander et al. |
| 2005/0010299 | A1 | 1/2005 | Disilvestro |
| 2007/0250286 | A1 | 10/2007 | Duncan et al. |
| 2008/0027296 | A1 | 1/2008 | Hadvary et al. |
| 2008/0311765 | A1 | 12/2008 | Chatterjee et al. |
| 2009/0309683 | A1 | 12/2009 | Cochran |
| 2010/0174189 | A1 | 7/2010 | Abraham |
| 2010/0228089 | A1 | 9/2010 | Hoffman et al. |
| 2011/0046558 | A1 | 2/2011 | Gravesen et al. |
| 2011/0208444 | A1* | 8/2011 | Solinsky ................ A61B 5/112 702/41 |
| 2011/0288379 | A1 | 11/2011 | Wu |
| 2013/0211259 | A1* | 8/2013 | Komistek ............ A61B 8/5223 600/440 |
| 2013/0217998 | A1 | 8/2013 | Mahfouz et al. |
| 2014/0049911 | A1 | 2/2014 | Corbin et al. |
| 2014/0114453 | A1 | 4/2014 | Bentley |
| 2014/0142864 | A1 | 5/2014 | Spears et al. |
| 2014/0275815 | A1 | 9/2014 | Stein et al. |
| 2014/0316526 | A1 | 10/2014 | Grotz |
| 2014/0358193 | A1* | 12/2014 | Lyons ................ A61N 1/36139 607/48 |
| 2015/0003699 | A1 | 1/2015 | Davis et al. |
| 2015/0045700 | A1 | 2/2015 | Cavanagh et al. |
| 2015/0230183 | A1 | 8/2015 | Stogaitis et al. |
| 2015/0238094 | A1 | 8/2015 | Lai et al. |
| 2016/0066843 | A1 | 3/2016 | Mensinger et al. |
| 2016/0220176 | A1 | 8/2016 | Desnerck et al. |
| 2016/0302721 | A1 | 10/2016 | Wiedenhoefer et al. |
| 2016/0310066 | A1 | 10/2016 | Wiedenhoefer et al. |

FOREIGN PATENT DOCUMENTS

| | | |
|---|---|---|
| WO | 2010/088696 | 8/2010 |
| WO | 2013/072234 | 5/2013 |
| WO | 2016/029138 | 2/2016 |

OTHER PUBLICATIONS

International Search Report and Written Opinion for PCT/US2016/023632 dated May 31, 2016.

Martinson et al., "Implementation of motion capture support in smartphones," Department of Computer Science and Engineering, Chalmers University of Technology. Jan. 1, 2010, Retrieved from the Internet at http://studentarbeten.chalmers.se/publication/129442-implementation-of-motion-capture-support-in-smartphones.

U.S. Appl. No. 15/422,312, Entitled: Systems and Methods Using a Wearable Device for Monitoring an Orthopedic Implant and Rehabilitation, Inventor: Wiedenhoefer et al., filed Feb. 1, 2017.

U.S. Appl. No. 15/422,320, Entitled: System and Methods With User Interfaces for Monitoring physical Therapy and Rehabilitation , Inventor: Wiedenhoefer et al., filed Feb. 1, 2017.

International Search Report and Written Opinion for PCT/US2018/016424 dated Mar. 28, 2018.

International Search Report and Written Opinion for PCT/US2018/016417 dated Mar. 29, 2018.

International Search Report and Written Opinion for PCT/US2018/016422 dated Apr. 16, 2018.

Official Communication for U.S. Appl. No. 15/077,809 dated Dec. 28, 2017.

Official Communication for U.S. Appl. No. 15/077,809 dated Jul. 2, 2019.

Official Communication for U.S. Appl. No. 15/077,809 dated Nov. 2, 2018.

Official Communication for U.S. Appl. No. 15/077,793 dated Jul. 15, 2019.

Official Communication for U.S. Appl. No. 15/077,793 dated Mar. 21, 2019.

Official Communication for U.S. Appl. No. 15/077,793 dated Oct. 25, 2018.

* cited by examiner

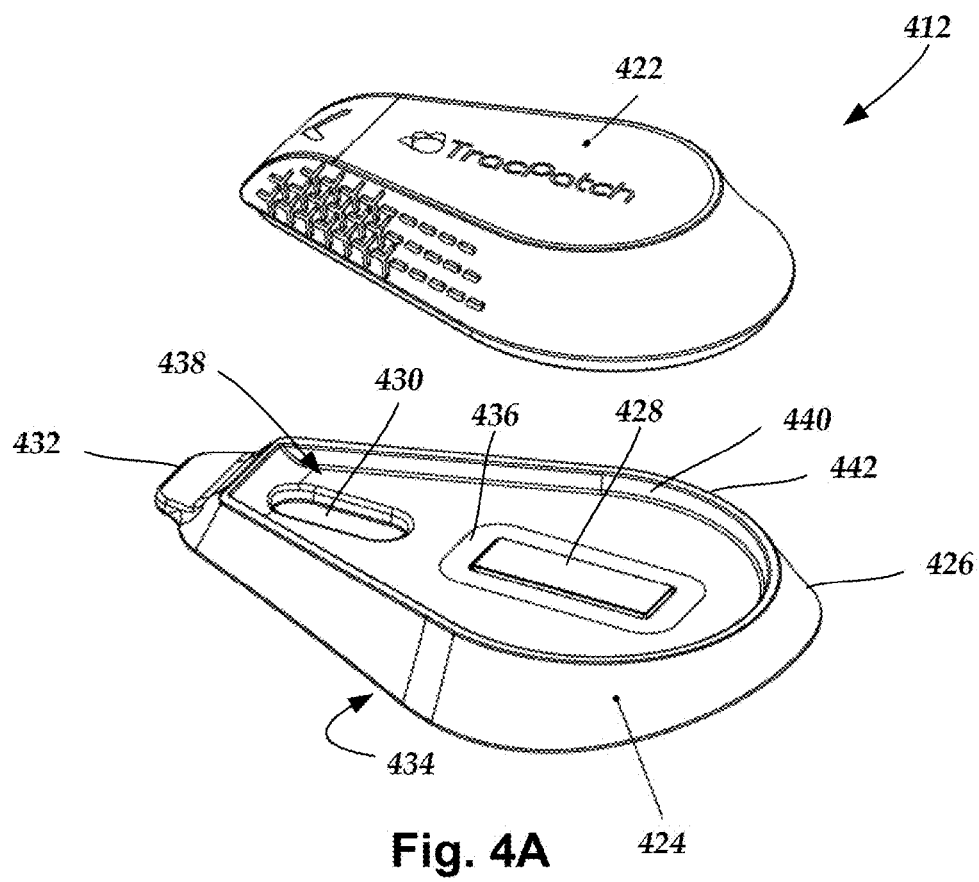
Fig. 4A
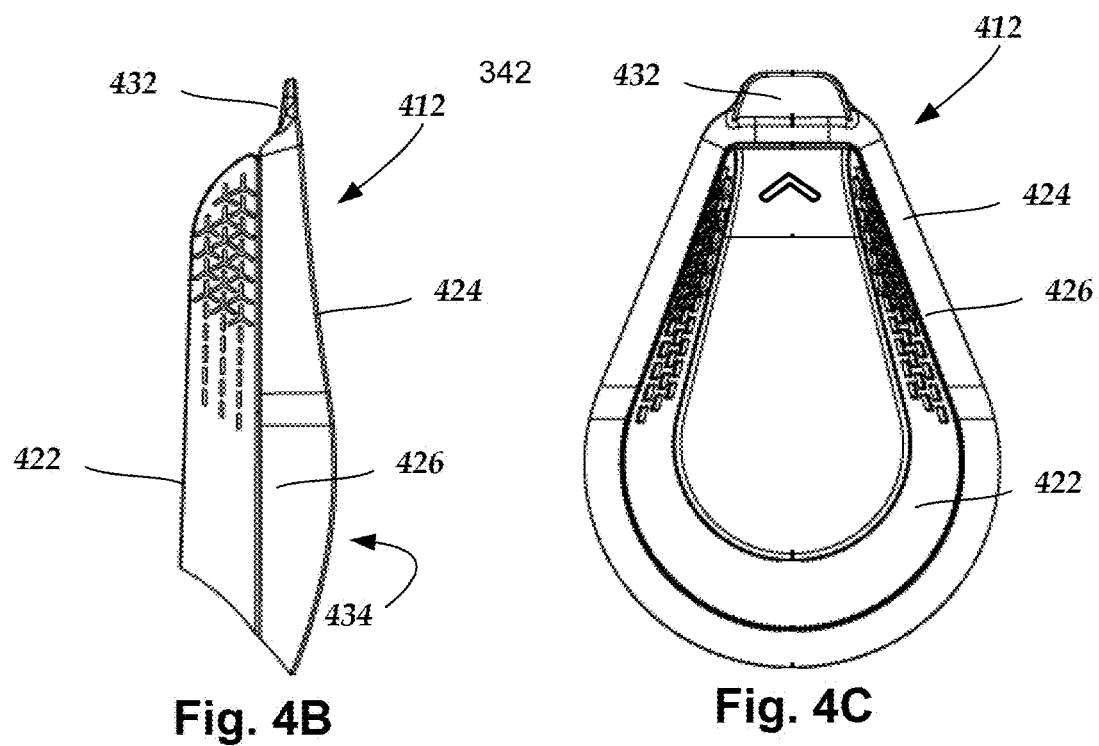
Fig. 4B
Fig. 4C

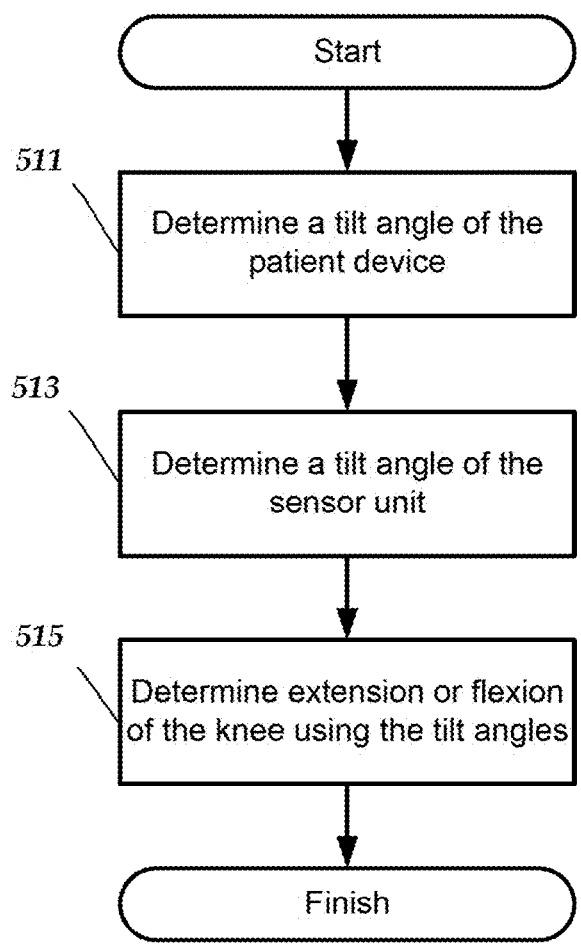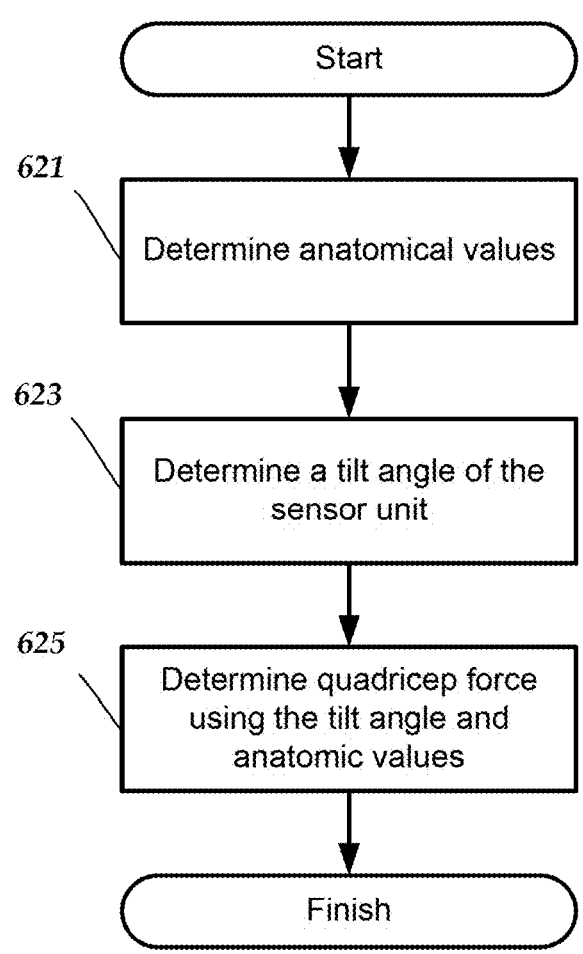
Fig. 5C
Fig. 6B

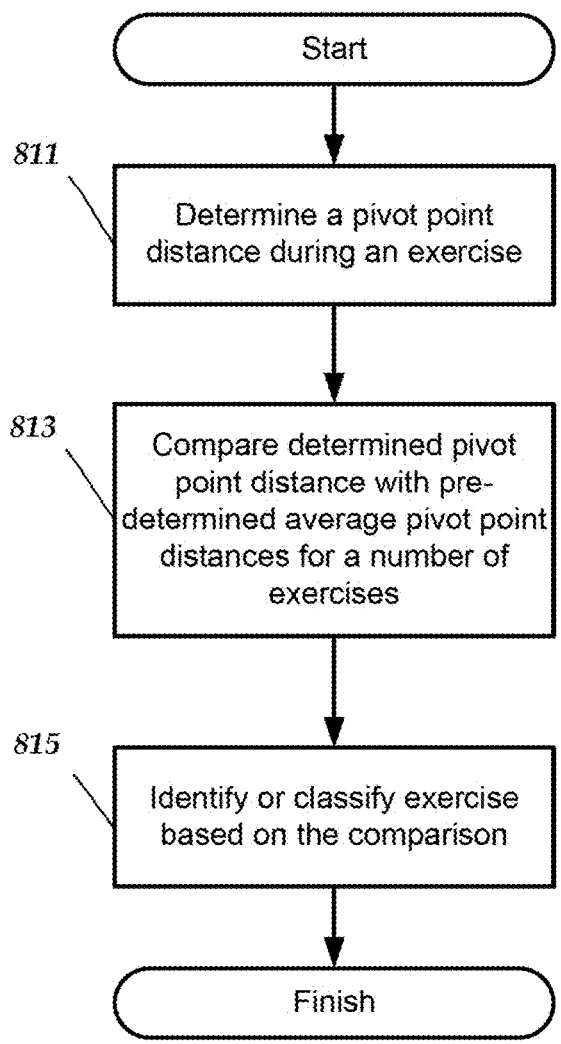
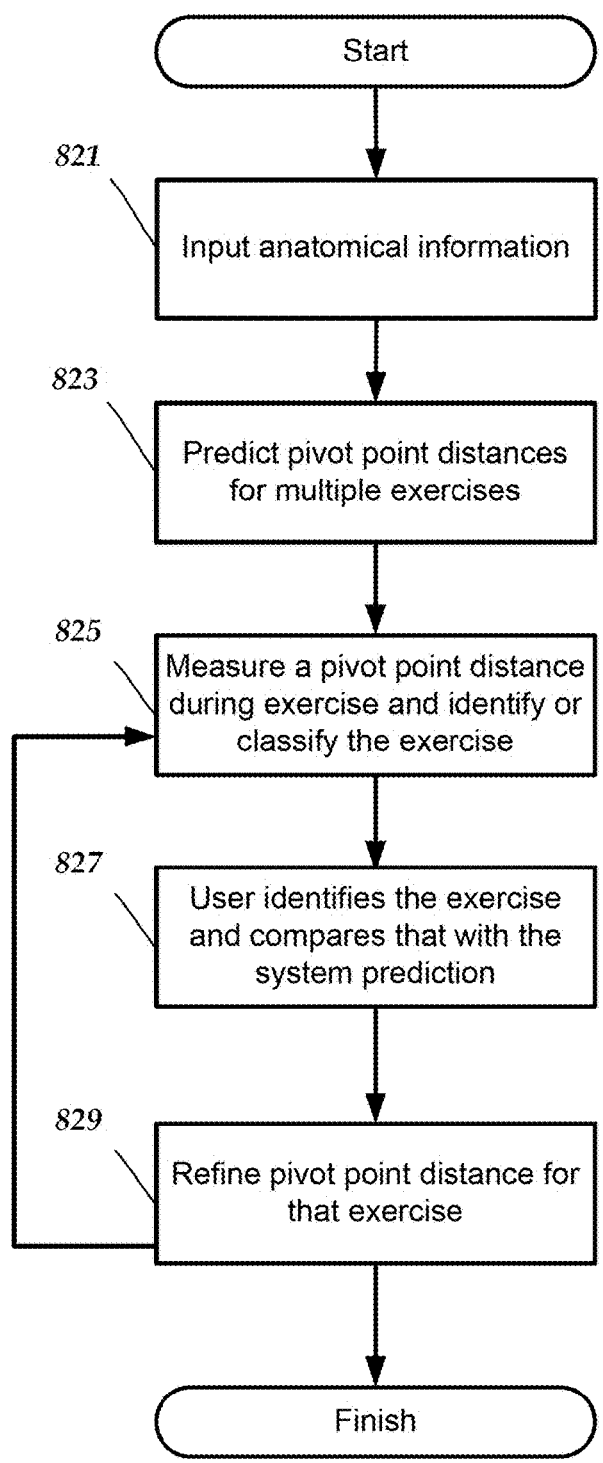
Fig. 8D
Fig. 8E

SYSTEM AND METHODS FOR MONITORING PHYSICAL THERAPY AND REHABILITATION OF JOINTS

CROSS-REFERENCE TO RELATED APPLICATION(S)

This application is a continuation-in-part of U.S. patent application Ser. No. 15/077,809, filed Mar. 22, 2016, which claims the benefit of both U.S. Provisional Patent Application Ser. No. 62/136,892, filed Mar. 23, 2015, and U.S. Provisional Patent Application Ser. No. 62/136,925, filed Mar. 23, 2015, all of which are incorporated herein by reference in their entirety.

FIELD

The present invention is directed to the area of physical therapy, orthopedic implants, and rehabilitation. The present invention is also directed to systems and methods for monitoring physical therapy and rehabilitation of joints.

BACKGROUND

Joint replacement surgery is a common orthopedic procedure for joints such as the shoulder, hip, knee, ankle, and wrist. In situations where the patient has worn-out or damaged a joint, it is possible to replace the joint with an implant that can merge with the skeletal structure and restore pain free movement and function. Prior to implanting prosthetic components in a joint of a patient, a surgeon generally resects at least a portion of the patient's native bone in order to create a platform, recess, or cavity for receiving at least a portion of the prosthetic components being implanted. During the process of implanting the prosthetic components muscles and tendons must be repositioned and reattached.

The patient must go through physical therapy in order to recover from this major surgery. The patient must exercise regularly as well as push for flexibility and balance in muscles that have been displaced. While the goal is to have the patient extend their range of motion, there can be an increased risk of falls or over-extension that can damage the implant and injure the patient. If the patient does not push their rehabilitation and achieve the needed range of motion, they will find themselves with a stiff joint which may require an additional surgical operation (MUA—Manipulation Under Anesthesia) to achieve an adequate range of motion to maintain their active lifestyle. Measuring or monitoring the progress of the physical therapy can be problematic but is very useful for maintaining the patient's dedication and participation.

BRIEF SUMMARY

One embodiment is a system for monitoring a patient. The system includes a sensor unit configured and arranged to be disposed on or within the patient, the sensor unit including an accelerometer and a communication arrangement. The system also includes a patient device configured and arranged for communication with the sensor unit. The patient device includes a display, a tilt angle sensor, a memory, and a processor coupled to the display and memory. The processor is configured and arranged for performing actions including determining a tilt angle of the patient device, when sitting on a thigh of the patient, using the tilt angle sensor of the patient device; obtaining a tilt angle of the sensor unit disposed on or within a portion of a leg of the patient below a knee of the patient; and determining an extension or flexion of the knee of the patient using the tilt angle of the patient device and the tilt angle of the sensor unit.

In at least some embodiments, obtaining the tilt angle of the sensor unit includes obtaining the tilt angle of the sensor unit that has been determined by the processor of the sensor unit. In at least some embodiments, obtaining the tilt angle of the sensor unit includes obtaining at least one position value of the accelerometer of the sensor unit and calculating the tilt angle from the at least one position value.

In at least some embodiments, determining the extension or flexion includes determining a maximum flexion of the knee using the tilt angle of the sensor unit at a maximum forward extension of the knee. In at least some embodiments, determining the extension or flexion includes determining a maximum extension of the knee using the tilt angle of the sensor unit at a maximum backward extension of the knee. In at least some embodiments, the actions further include determining an estimated quadricep force using the tilt angle of the sensor unit.

Another embodiment is a system for monitoring a patient. The system includes at least one sensor unit configured and arranged to be disposed on or within the patient, the at least one sensor unit, in combination, including at least two accelerometers and a communication arrangement. The system also includes a patient device configured and arranged for communication with the at least one sensor unit. The patient device includes a display, a memory, and a processor coupled to the display and memory. The processor is configured and arranged for performing actions including, during performance of an exercise, obtaining a pivot point distance using the at least two accelerometers of the at least one sensor unit; comparing the determined pivot point distance with pre-determined pivot point distances for a plurality of exercises; and, based on the comparison, identifying the exercise being performed as a one of the plurality of exercises.

In at least some embodiments, obtaining the pivot point distance includes obtaining the pivot point distance that has been determined by the processor of at least one of the at least one sensor unit. In at least some embodiments, obtaining the pivot point distance includes obtaining at least one position value from each of two of the accelerometers and calculating the pivot point distance from the obtained position values. In at least some embodiments, obtaining a pivot point distance includes obtaining an average pivot point distance over a period of time.

In at least some embodiments, the pre-determined pivot point distances for the plurality of exercises are average pivot point distances for the plurality of exercises for a population of patients. In at least some embodiments, the pre-determined pivot point distances for the plurality of exercises are determined from one or more anatomical measurements of the patient. In at least some embodiments, the actions further including determining a number of repetitions of the exercise being performed.

Yet another embodiment is a system for monitoring a patient. The system includes at least one sensor unit configured and arranged to be disposed on or within the patient, the at least one sensor unit, in combination, including at least two accelerometers and a communication arrangement. The system also includes a patient device configured and arranged for communication with the at least one sensor unit. The patient device includes a display, a memory, and a processor coupled to the display and memory. The processor is configured and arranged for performing actions including a) predicting average pivot point distances for a plurality of exercises; b) during performance of a one of the exercises, obtaining a pivot point distance using the at least two accelerometers of the at least one sensor unit; c) using the predicted average pivot point distances, identifying the exercise being performed; and d) refining the predicted average pivot point distance for the exercise being performed with the obtained pivot point distance.

In at least some embodiments, the actions further include repeating steps b)-d) for the one of the exercises, using the refined predicted average pivot point distance instead of the predicted average pivot point distance. In at least some embodiments, the actions further include repeating steps b)-d) for an additional one or more of the exercises.

In at least some embodiments, obtaining the pivot point distance includes obtaining the pivot point distance that has been determined by the processor of at least one of the at least one sensor unit. In at least some embodiments, obtaining the pivot point distance includes obtaining at least one position value from each of two of the accelerometers and calculating the pivot point distance from the obtained position values.

In at least some embodiments, the actions further include obtaining anatomical information for the patient, wherein predicting average pivot point distances for a plurality of exercises includes predicting the average pivot point distances for the plurality of exercises using the anatomical information. In at least some embodiments, the anatomical information includes a height of the patient.

Yet another embodiment is a method for performing the actions recited for any of the systems described above. A further embodiment is a non-transitory computer readable medium comprising instructions for performing the actions recited for any of the systems described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a perspective side view of another embodiment of a sensor unit and a base disengaged from each other, according to the invention;

FIG. 4B is a side view of the sensor unit and base of FIG. 4A engaged with each other, according to the invention;

FIG. 4C is a top view of the sensor unit and base of FIG. 4A engaged with each other, according to the invention;

FIG. 5C is a flowchart of one embodiment of a method for determining extension and flexion; according to the invention;

FIG. 6B is a flowchart of one embodiment of a method for determining quadricep force; according to the invention;

FIG. 8D is a flowchart of one embodiment of a method for identifying or classifying exercises using pivot point distance; according to the invention;

FIG. 8E is a flowchart of one embodiment of a method for refining average pivot point distances for use in the method of FIG. 8D; according to the invention;

DETAILED DESCRIPTION

The present invention is directed to the area of physical therapy, orthopedic implants, and rehabilitation. The present invention is also directed to systems and methods for monitoring physical therapy and rehabilitation of joints.

A system, as described herein, can be used to monitor physical therapy or the healing process or rehabilitation of the patient after surgery, as well as monitor or verify the extent of the patient's activity. The system includes one or more sensors that can communicate with a processor that can produce information, based on the sensor readings and data, that can facilitate the patient or another user, such as a clinician, doctor, physical therapist, nurse, care coordinator, or other appropriate person, monitoring the patient's activity, the status of an orthopedic implant or surrounding tissues, or the effects of rehabilitation or other therapy. It will be understood, however, that the systems, devices, and methods described herein can be used in the context of other surgeries or even rehabilitation or physical therapy without surgical intervention. The sensors, described below, are placed near a physical therapy or rehabilitation site, such as a surgical site or the body portion to be rehabilitated.

The system may also provide alerts if patient tissue becomes inflamed or if the effectiveness of, or compliance to, physical or rehabilitation therapy is insufficient. The system includes a wearable device with one or more sensors. For example, one or more sensors may be provided on a wearable device that is applied to the skin of the patient.

In at least some embodiments, the one or more sensors communicate with a sensor processor on the device containing the sensors. In at least some embodiments, the sensor processor, or, alternatively or additionally, the sensors, communicate with a processor of a patient device, such as a mobile phone, tablet, computer or the like, or with a processor of a clinician device, such as a mobile phone, tablet, computer or the like.

Figure 1:
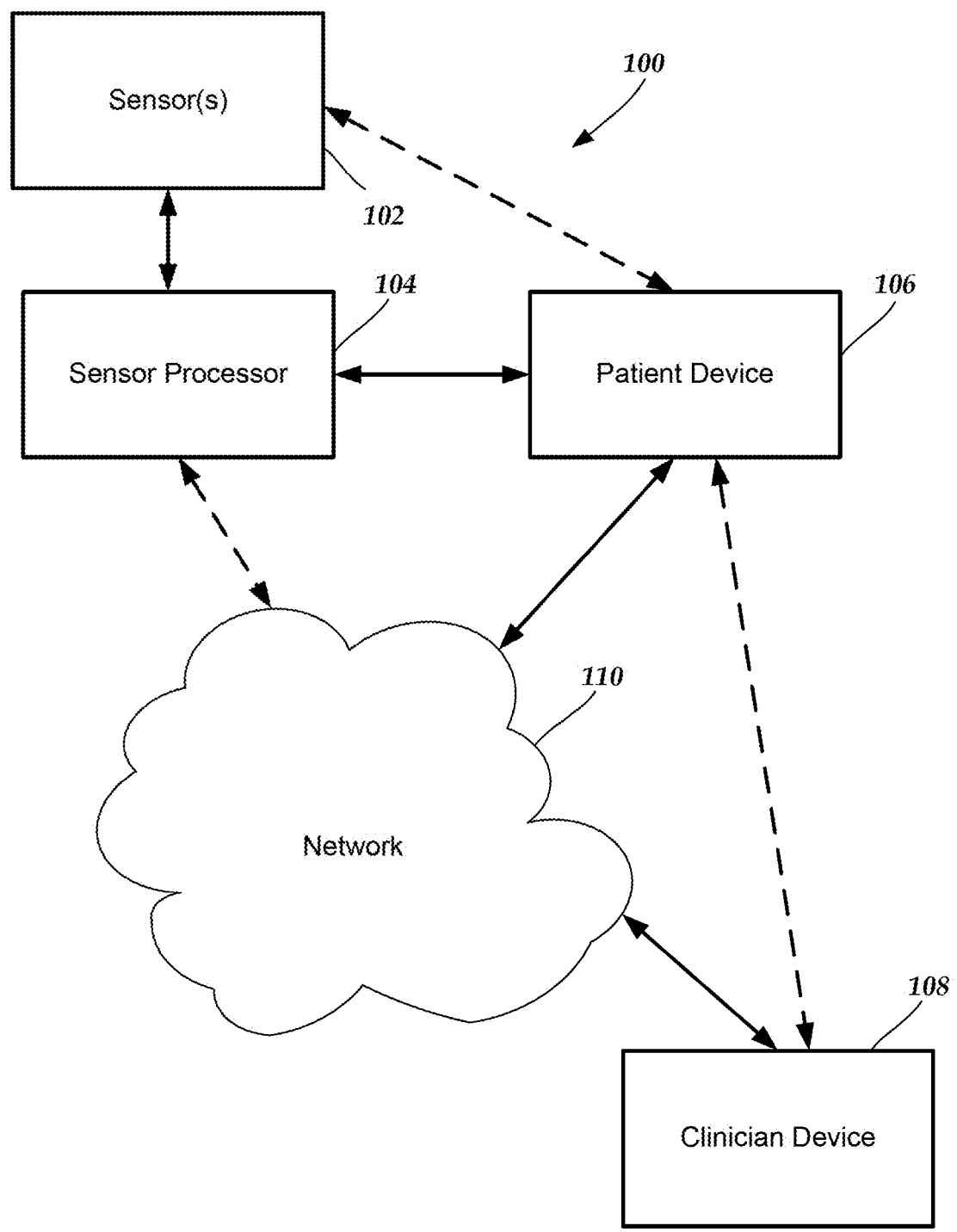
FIG. 1 is a schematic diagram of one embodiment of a system for monitoring rehabilitation of a patient after implant surgery, according to the invention.

FIG. 1 illustrates one embodiment of a system 100 for monitoring an orthopedic implant and rehabilitation after orthopedic replacement surgery. The system 100 includes one or more sensors 102, an optional sensor processor 104, a patient device 106 (such as a mobile phone, tablet, computer or the like), a clinician device 108, and a network 60. In at least some embodiments, the one or more sensors 102 and, preferably, the sensor processor 104 (or one or more of multiple sensor processors) are provided in a wearable device 112 that is external to the patient such as, for example, a device that is applied to the skin of the patient or is carried in a brace or other article or textile that is worn by the patient. Alternatively, one or more of the sensors 102 and, optionally, the sensor processor can be implanted in the patient. In some embodiments, one or more of the sensors 102 are implanted and a sensor processor and, optionally, one or more additional sensors are provided in a wearable device.

Other embodiments of the system may include fewer or more components than those illustrated in FIG. 1, but the system typically includes the sensor(s) 102 and a processor (such as sensor processor 104, patient device 106, or clinician device 108) to communicate with the sensor(s) and provide information based on the sensor data. In the illustrated embodiment, the wearable device 112 includes the sensors 102 and sensor processor 104, but it will be understood that other sensors may be included that are not part of the wearable device 112. For example, one or more additional sensors may be combined into another wearable device that may also include a sensor processor. It will also be understood that, in some embodiments, the wearable device 102 may not include a sensor processor 104 or the sensor processor 104 may have limited capabilities (such as, for example, obtaining and transmitting sensor readings without (or with limited) analysis of the sensor readings.

In FIG. 1, the solid lines indicate communication between components in at least some embodiments of the system. Dotted lines indicate alternative or additional modes of communication between components. In addition to the communication illustrated in FIG. 1, in at least some embodiments, the sensor processor 104 or sensors 102 may also communicate directly with the clinician device. Communications can include, but is not limited to, wireless communication, wired communication, optical communication, ultrasonic communication, or the combination thereof. Satellite communication, cellular communication, Bluetooth™, near field communications (NFC), Infrared Data Association standard (IrDA), wireless fidelity (WiFi), and worldwide interoperability for microwave access (WiMAX) are non-limiting examples of wireless communication that can be used for communications. Ethernet, digital subscriber line (DSL), fiber to the home (FTTH), and plain old telephone service (POTS) are non-limiting examples of wired communication that can be used for communications.

The network 60 can be any suitable type of network including, but not limited to, a personal area network (PAN), local area network (LAN), metropolitan area network (MAN), wide area network (WAN), the Internet, or any combination thereof. In at least some embodiments, the network 60 can be bypassed to provide direct connection between components. It will be understood that other devices, such as a server or server farm, memory storage device, or the like can be connected to the patient device 106 or clinician device 108 through the network 60 or directly. For example, a server may be coupled to the patient device 106 or clinician device 108 that stores patient or other medical information, applications, user interfaces, a web interface, or the like for access by the patient device 106 or clinician device 108.

The patient device 106 and the clinician device 108 can be any of a variety of devices, such as computers (for example, a notebook computer, a mobile medical station or computer, a server, a mainframe computer, or a desktop computer), mobile devices (for example, a cellular phone or smartphone, personal digital assistant, or a tablet), or any other suitable device. In at least some embodiments, the clinician device 108 can be incorporated into a medical station or system.

Figure 2:
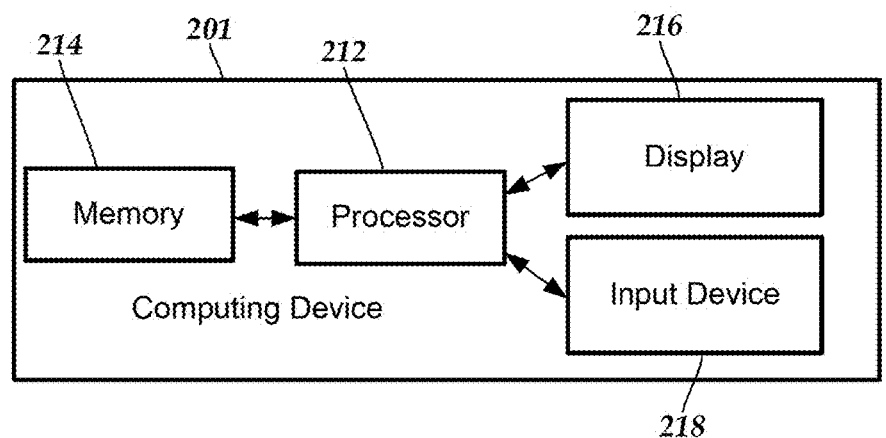
FIG. 2 is a schematic diagram of one embodiment of a computing device for use in the system of FIG. 1, according to the invention.

FIG. 2 illustrates one embodiment of a computing device 201 for use as the patient device 106 or clinician device 108. The computing device 201 includes a processor 214 and a memory 216, a display 218, and an input device 220. The computing device 201 can be local to the user or can include components that are non-local to the computer including one or both of the processor 214 or memory 216 (or portions thereof). For example, in some embodiments, the user may operate a terminal that is connected to a non-local processor or memory.

The computing device 201 can utilize any suitable processor 214 including one or more hardware processors that may be local to the user or non-local to the user or other components of the computing device. The processor 214 is configured to execute instructions provided to the processor. Such instructions can include any of the steps of methods or processes described herein.

Any suitable memory 216 can be used for the computing device 214. The memory 216 illustrates a type of computer-readable media, namely computer-readable storage media. Computer-readable storage media may include, but is not limited to, nonvolatile, non-transitory, removable, and non-removable computer-readable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal.

By way of example, communication media includes wired media such as twisted pair, coaxial cable, fiber optics, wave guides, and other wired media and wireless media such as acoustic, RF, infrared, Bluetooth™, near field communication, and other wireless media.

The display 218 can be any suitable display device, such as a monitor, screen, display, or the like, and can include a printer. The input device 220 can be, for example, a keyboard, mouse, touch screen, track ball, joystick, voice recognition system, camera, microphone, or any combination thereof, or the like.

Returning to FIG. 1, the sensor processor 104 can be any suitable processor including one or more hardware processors. The sensor processor 104 is configured to execute instructions provided to the processor. The sensor processor 104 is configured to receive sensor data from the sensor(s) and communicate with the patient device 106, network 60, clinician device 108, or any combination thereof. Optionally, the sensor processor 104 may also process or analyze the sensor data and may have instructions stored thereon to perform such processing or analysis including, for example, instructions to perform the steps of any of the processing or analysis described herein. In at least some embodiments, one or more of the sensor(s) 102 can each include a processor that perhaps some or all of the functions of the sensor processor 104.

The one or more sensors 102 are provided to monitor an orthopedic implant and surrounding tissue or monitor rehabilitation after orthopedic surgery whether an implant was required or not, or to provide preparatory therapy in advance of a surgery, or any combination thereof. This disclosure will use an orthopedic knee implant as an example, but it will be understood that other joint implants, such as, for example, implants for the shoulder, hip, ankle, wrist, or any other joint, or any other orthopedic device, such as an orthopedic spinal implant, whether joint replacement, joint resurfacing, soft tissue reconstruction, debridement, limb correction surgery, ligament replacement, or the like.

Any suitable type of sensor 102 can be used including, but not limited to, accelerometers, magnetometers, gyroscopes, proximity sensors, infrared sensors, ultrasound sensors, thermistors or other temperature sensors, cameras, piezoelectric or other pressure sensors, sonar sensors, external fluid sensor, skin discoloration sensor, pH sensor, microphone, or the like or any combination thereof. In at least some embodiments, the system 100 includes at least one, two, three, four, five, six, or more different types of sensors 102. The system may include at least one, two, three, four, five, six, eight, ten, or more sensors 102. Further examples of suitable sensors and their arrangement and use can be found at U.S. patent application Ser. Nos. 15/077,809 and 15/077,793 and U.S. Provisional Patent Applications Ser. Nos. 62/136,892 and 62/136,925, all of which are incorporated herein by reference.

The one or more sensors 102 can be used to measure, monitor, or otherwise observe one or more aspects of the orthopedic device, surrounding tissue, or patient activity, or the like. The following are examples of observations or measurements that can be made or interpreted using one or more of the sensors: number of steps, repetitions of an exercise, repetitions of joint movement (e.g., joint pivoting), type of exercise being performed, or other actions; stability, or lack thereof; flexion angle or range of motion; rate of motion; temperature of skin; pulse or pulse profile or heart rate recovery time after activity; ultrasound images, flow measurements, or Doppler measurements; sonar images, flow measurements, or Doppler measurements; pressure or load bearing measurements; detection of a limp or body orientation (e.g., subluxation, posture, scoliosis) or a change in body orientation; joint shock or impact monitoring; sleep profile or rest duration; gait analysis, body/limb/joint alignments; or the like. A system 100 can observe or measure one or more of these items or any combination of the items.

The following provides further details on some of these measurements or observations. One or more sensors (for example, accelerometers, gyroscopes, magnetometers, proximity sensors, or the like) may count steps or repetitions of an exercise or number of joint movements or other actions experienced by the sensor, and may be utilized to determine what type of exercise or movement is occurring. This can be used, for example, to monitor patient activity, monitor compliance with exercise therapy, or monitor possible signs of pain or other conditions that may hinder or aid rehabilitation. The sensor data may also be used to monitor changes in activity or trends in activity.

One or more sensors (for example, accelerometers, gyroscopes, magnetometers, proximity sensors, or the like) may sense or detect or compute the range of motion of the sensor, joint, or other portion of the patient body or the flexion of the joint. This can be used, for example, to monitor patient rehabilitation, patient activity, monitor compliance with exercise therapy, or monitor possible signs of pain or other conditions that may hinder or aid rehabilitation. These sensors or other sensors may be used to monitor shock to, or impact on, the orthopedic device or tissue around the orthopedic device. The sensor data may also be used to monitor changes in range of motion or flexion or trends in range of motion or flexion.

As an illustrative example, two proximity sensors (for example, a magnetometer and a magnet—such as a permanent magnet, electromagnet, or polymagnet or the like) can be implanted or placed externally on opposing sides of a joint. The distance between the two proximity sensors can be detected, measured, or otherwise observed. The distance between the two proximity sensors can be correlated to flexion or range of motion of the patient's joint. The variation in the distance between the two proximity sensors can be used to measure number of repetitions of joint motion or to monitor compliance with patient therapy. The variation in distance among repetitions or the trend in the variation among repetitions may be used to monitor improvement in joint flexibility or may indicate pain or other deleterious physical conditions of orthopedic implant or surrounding tissue. This information can be used to measure progress in the physical therapy following the surgery.

As another illustrative example, one or more accelerometers can measure the acceleration from joint movement. A ratio of measured acceleration between accelerometers of known distance apart can be used to assess the joint movement and region of motion or flexion by calculating the center of rotation about which the device is being rotated. This information can be used for the same purposes as described in the preceding example.

In another illustrative example, 1) an accelerometer and 2) a gyroscope or magnetometer (which indicates direction relative to magnetic north) can be used to measure range of motion, rate of motion, number of repetitions, or the like. This information can be used for the same purposes as described in the preceding two examples.

In another illustrative example, a single sensor such as an accelerometer, gyroscope, or magnetometer can be used to measure or otherwise observe range of motion, rate of motion, number of repetitions, or the like. In at least some embodiments, these measurements or other observations are determined using the sensor data and one or more assumptions about the sensor or sensor data based on, for example, the recognition of patterns in the sensor data, the upper and lower limits of the range in the data collected, or the like. Such information can be used in a manner similar to that in the preceding three examples.

One or more sensors (for example, thermistors or infrared sensors) may sense or detect or compute a temperature or a change in temperature or a temperature trend. The temperature may be a skin temperature or ambient temperature. The temperature measurements may be used, for example, to indicate the possibility of inflammation or pain or another condition that may hinder rehabilitation or patient health. The temperature measurement may also be used, for example, to monitor if icing is being performed effectively, which can help reduce inflammation and aid healing. These sensors may also or alternatively be used to sense, detect, or measure a pulse, a change in pulse, trends in the patient's pulse, a pulse profile, or heart rate recovery after patient activity (such as exercise or other exertion).

One or more sensors (for example, ultrasound or sonar sensors or cameras or the like) can sense or detect or compute particles or density of particles or a particle density trend. These sensors may also be used to sense the tissue surrounding the orthopedic device, detect wear or dimensional changes on the orthopedic device or surrounding tissue, or the like. Ultrasound and sonar sensors may also be used to determine how close other parts of the knee (or other joint) are to the implant.

One or more sensors (for example, piezoelectric, strain gage, or other pressure or load bearing sensors) can sense or detect or compute pressure or load with or around the sensor or orthopedic device. The sensor data may also be used to monitor changes in range of pressure or load bearing or trends in pressure or load bearing. These sensors or other sensors may be used to monitor shock to, or impact on, the orthopedic device or tissue around the orthopedic device. A pressure or load bearing sensor may also be used to detect swelling of the tissue around the orthopedic implant. Multiple pressure or load bearing sensors may also be used to detect flexion (which may be indicated by a uniaxial stretching of the tissue) and swelling (which may be indicated by biaxial stretching of the tissue.)

U.S. patent application Ser. Nos. 15/077,809 and 15/077,793 and U.S. Provisional Patent Applications Ser. Nos. 62/136,892 and 62/136,925, all of which are incorporated herein by reference, describe examples of sensors (including arrangements with implantable sensors), systems, devices, and methods for monitoring rehabilitation. Further examples of sensors and their use can be found in U.S. patent application Ser. No. 15/422,312, entitled "Systems and Methods using a Wearable Device for Monitoring an Orthopedic Implant and Rehabilitation", and U.S. patent application Ser. No. 15/422,320, entitled "Systems and Methods with User Interfaces for Monitoring Physical Therapy and Rehabilitation", both of which are filed on even date herewith and incorporated herein by reference.

Power can be provided to the sensors 102 and optional sensor processor 104 using any suitable power source including, but not limited to, primary cells, rechargeable batteries, storage capacitors, other power storage devices, or the like or any combination thereof. In some embodiments, the power can be provided by a kinetic energy power source that utilizes the movements of the patient's body to generate power for the components or to or to charge a battery or storage capacitor or other power storage device coupled to the components. In some embodiments, wireless power sources can be used in place of (or in addition to) the battery, storage capacitor, or other power storage device.

In addition, a charging port can be provided for charging the battery or storage capacitor or other power storage device from a source such as a wall socket. Alternatively or additionally, wireless charging systems and methods can also be used. It will be understood that in some embodiments there may be multiple methods for providing power to the component or to a power storage device associated with the component. All of the sensors and optional sensor processor may be coupled to the same power source or some of the sensors (or even all of the sensors) and sensor processor may have individual power sources.

In at least some embodiments, the sensors and optional sensor processor can be active at all times to measure, monitor, or otherwise observe. In other embodiments, one or more of the sensors and optional sensor processor can be active periodically (with a period of, for example, 15 or 30 seconds or 1, 5, 10, 15, or 30 minutes or 1, 2, 3, 4, 6, 7, or 24 hours) or randomly to measure, monitor, or otherwise observe. Optionally, the period may be programmable. In addition, the period may be optionally altered based on data from one or more of the sensors. In yet other embodiments, one or more of the sensors and optional sensor processor may be activated manually or automatically by the sensor module, patient device, clinician device, or other device. In at least some embodiments, the sensors and optional sensor processor may have different activation schedules (continuous, periodic, random, or manual). For example, a sensor to measure temperature may do so periodically, a sensor to measure number of steps or movement of the joint may be continuous, and a sensor to measure range of motion may be activated manually by the wearable device, patient device, or clinician device when the patient performs rehabilitation exercises.

The systems and methods will be described herein with reference to an orthopedic knee implant or other knee surgery. Similar systems and methods can be used with other joints including, but not limited to, the finger joint, wrist joint, elbow joint, shoulder joint, hip joint, ankle joint, or toe joint. The systems and methods can be used to monitor physical therapy for any reason including, but not limited to, rehabilitation associated with other treatments including treatments for ligament or fracture surgery.

Figure 3A:
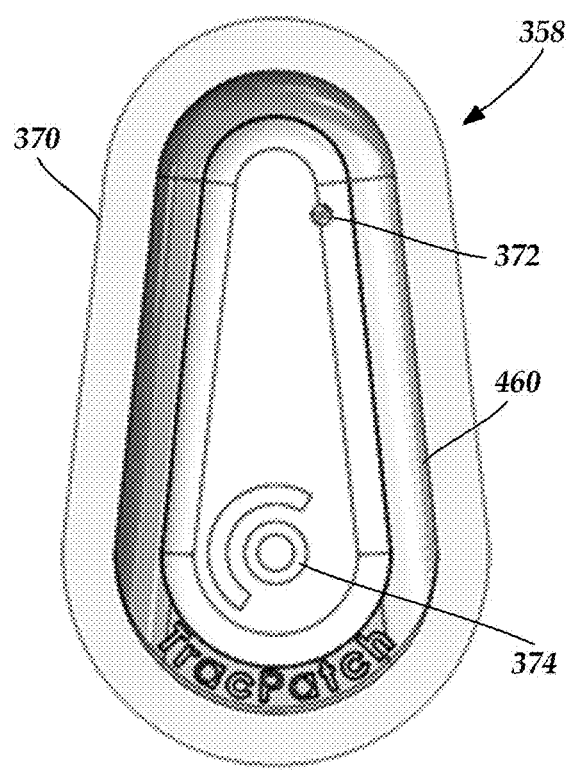
FIG. 3A is a top view of one embodiment of a sensor module that contains sensors for monitoring rehabilitation of a patient, according to the invention.
Figure 3B:
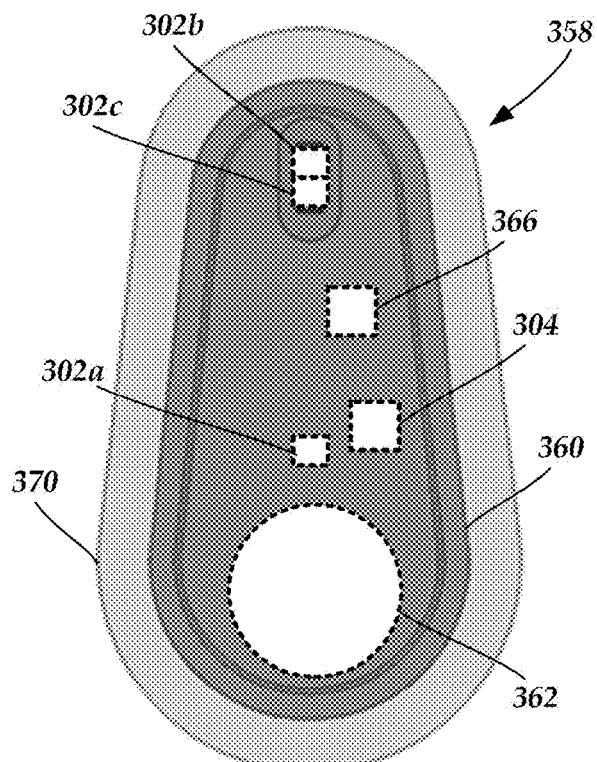
FIG. 3B is a bottom view of the sensor module of FIG. 3A, according to the invention.

FIGS. 3A and 3B are top and bottom views, respectively, of one embodiment of a sensor unit 358 that can be adhered, or otherwise placed adjacent, to the skin of the patient. The sensor unit includes a housing 360, optional adhesive pad 370, sensors 302a, 302b, 302c, power source 362, communications unit 366, and sensor processor 304. It will be recognized that other sensor units may have more or fewer sensors and that the sensors may be the same or of different types.

The housing 360 can be made of any suitable material, such as plastic materials (for example, silicone), and preferably has sufficient flexibility to fit comfortably on the patient's skin following the anatomical contours and to also flex as the patient moves. In at least some embodiments, the housing 360 is also water resistant to resist ingress of sweat, rain, and other fluids into the interior of the housing. In at least some embodiments, the housing 360 is sufficiently water resistant to allow the patient to shower with the sensor unit 358 remaining attached to the skin of the patient and without any covering over the sensor unit. In some embodiments, the housing 360 is sufficiently water resistant to allow the patient to bathe or swim without any covering over the sensor unit 358.

In at least some embodiments, the housing 360 has a shape or indicia on the housing that visually indicates or suggests the orientation of the device when the housing is attached to the patient. In the illustrated embodiment, one end of the device is narrower than the other end which indicates or suggests to the user that the narrow end is pointed toward the knee or other joint.

The illustrated embodiment also features a power light 372 that is lit when the sensor unit 358 is functioning to assure the patient that the device is operating. In some embodiments, the power light 372 may also flash or change color to indicate device functions such as, for example, a low battery, pairing with another device (for example, the patient device 106, clinician device 108, or network 110 of FIG. 1), actively taking readings using one or more of the sensors (particularly for sensors that are manually or periodically activated), alert the patient that it is time to perform exercises, change adhesives or the like.

The illustrated embodiment also features a power button 374 that can be activated to turn the device on and, optionally, to turn the device off. In at least some embodiments, the power button 374 may also be activated to manually direct one or more of the sensors to take readings.

The optional adhesive pad 370 is designed to hold the sensor unit 358 on the patient's skin. The adhesive pad 370 can have, for example, a substrate with adhesive on both sides of the substrate so that one side can be adhered to the patient's skin and the other side adhered to the housing 360. In at least some embodiments, the adhesive pad 370 can be periodically replaced (for example, every 1, 2, 5, or 3 days or every 2, 3, 4, or more weeks) as the adhesive next to the patient's skin or the housing 360 may degrade or otherwise lose some or all of its adhesiveness. Preferably, at least the adhesive to be adhered to the patient's skin is selected to prevent or resist causing skin irritation. Preferably, the adhesive on both sides of the substrate is selected to be water resistant and resist losing adherence due to contact with sweat. In at least some embodiments, the adhesive pad 370 extends around the circumference of the sensor unit 358, but includes one or more openings so allow the housing 360 to make contact with the skin of the patient or access to the patient without an intervening portion of the adhesive pad 370.

In other embodiments, instead of the adhesive pad 370, adhesive may be applied directly to the housing for adhering the housing with the directly to the skin. In yet other embodiments, instead of adhering the sensor unit to the skin, the sensor unit can be inserted into a brace or other item to be worn by the patient and hold the sensor unit in place at the desired position on the body. This wearable item, such as a brace, optionally includes an opening that allows the sensor unit to make contact with the skin of the patient.

The sensors 302a, 302b, 302c, power source 362, communications unit 366, and sensor processor 304 can be disposed within the housing 360. In some embodiments, a portion of one or more of the sensors, such as a temperature, pulse, or pressure sensor; moisture sensor, strain gage, may extend through the housing to provide contact with the skin or access to the patient without an intervening portion of the housing 360 or other parts of the sensor unit 358. In some embodiments of the sensor unit 358, sensor 302a is an accelerometer, sensor 302b is a gyroscope, and sensor 302c is a temperature sensor. The temperature sensor can be, for example, a thermistor or an infrared sensor. The accelerometer 302a and gyroscope 302b can be used to measure range of motion, number of steps, type of exercise, number of exercise repetitions or joint movements, and the like. In other embodiments, the sensors 302a, 302b can both be accelerometers that are optionally in-line with each other to increase accuracy in range of motion observations, and can be further utilized in the calculation of the point about which the motion is rotating. Yet other embodiments, the sensors include an accelerometer, a magnetometer, and a temperature sensor. As will be understood, any suitable sensor described above can be included in the sensor unit and any combination of those sensors can be used in the sensor unit. It is also understood that multiple sensor units can be utilized together to provide data refinement or to provide comparative information, such as to show improvement in limp, or more accurately define the positions of both sides of the joint.

Any of the power sources described above can be used for a power source 362. For example, the power source 362 can be a primary cell and may have an expected lifetime under normal usage of at least 1, 2, or 4 weeks or at least 1, 2, 3, 4, 6, 8, 10, 12, 15, 18, 24, months or more. In some embodiments, the power source 362 is rechargeable using, for example, a recharge port in the sensor unit 358 or is capable of being wirelessly charged such as with an inductive recharge device (such as an inductive mat or sleeve), or using WiFi or ultrasonic charging as described above. The power could be provided to the device by energy harvesting means, such as with cantilevered piezo reeds, a generator and pendulum setup, passive magnets rolling/sliding/bouncing through or by coils, or the like to convert some amount of kinetic energy into electrical energy to be used by the device. The power source 362 provides power to the sensors 302a, 302b, 302c, communications unit 366, sensor processor 304, and any other components in the sensor unit.

The sensor processor 304 can be any suitable processor and may include, or be coupled to, a memory unit for storing sensor data. The sensor processor 304 can be wired or wirelessly coupled to the sensor 302a, 302b, 302c for receiving data from the sensors. In some embodiments, the sensor processor 304 may include analysis algorithms for analyzing or partially analyzing the sensor data. In other embodiments, the sensor processor 304 may be primarily designed to receive, store, and transmit sensor data.

The communications unit 366 can be any suitable communications arrangement that can transmit information from the sensor processor 304 or sensors 302a, 302b, 302c to another device (such as the patient device 106, clinician device 108, or network 110 of FIG. 1.) The communications unit 366 can transmit this information by any suitable wired or wireless technique including, but not limited to, Bluetooth™, near field communications, WiFi, infrared, radio frequency, acoustic, optical, or using a wired connection through a data port in the sensor unit or any other communications technique presented herein or the like.

Additional examples of sensor units, including implantable sensor units, can be found at, for example, U.S. patent application Ser. Nos. 15/077,809 and 15/077,792 and U.S.

Provisional Patent Applications Ser. Nos. 62/136,892 and 62/136,925, all of which are incorporated herein by reference.

Figure 4D:
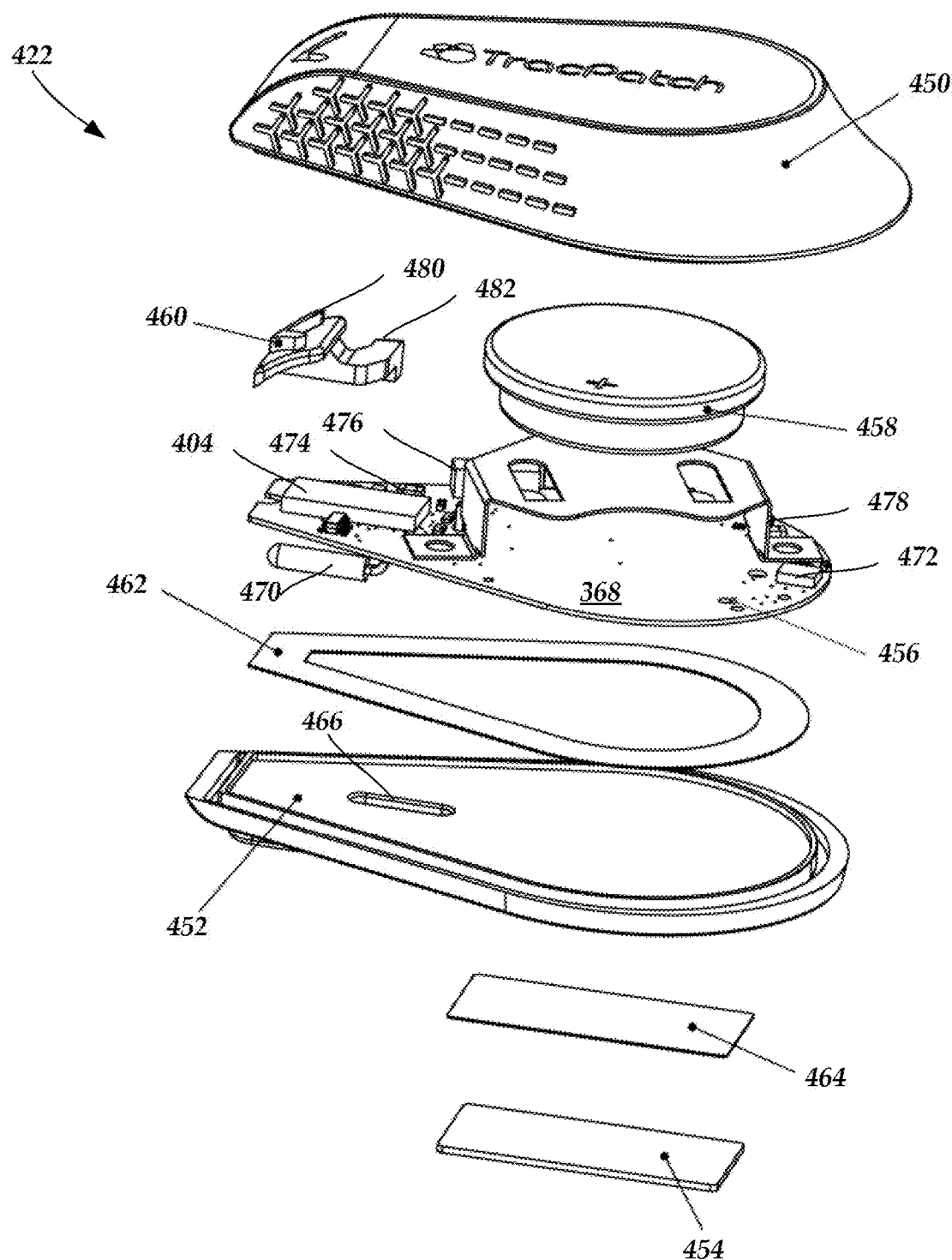
FIG. 4D is an exploded view of the sensor unit of FIG. 4A, according to the invention.

FIGS. 4A-4E illustrate one embodiment of a wearable device 412 that includes a sensor unit 422 and a base 424. The sensor unit 422 is removable from the base 424, as illustrated in FIG. 4A. The wearable device 412, as illustrated in FIGS. 4B and 4C, is disposed on the patient's skin with the base 424 adhered to the skin.

The base 424 includes a flexible receiving shell 426, a magnet 428, an optional opening 430 for a temperature sensor, an optional tab 432, adhesive disposed on a bottom surface 434 of the shell, and an optional magnet holder 436 disposed on the shell. The magnet 428 of the base 424 magnetically attaches to a similar magnet 454 (FIG. 4C) in the sensor unit 422 when the sensor unit 422 is attached to the base 424. The magnets 428, 454 are intended to maintain attachment of the sensor unit 422 to the base 424 during normal activity, exercise, and other physical therapy unless a patient or other person disengages the sensor unit from the base. Optionally, a magnet holder 436 fits over (entirely or only a perimeter of) the magnet 428 to hold the magnet to the shell 426.

In at least some embodiments, the shell 426 of the base 424 is sufficiently flexible for adhesion to the skin of a patient as the patient moves during normal activity or physical therapy exercises. The shell may be made of any suitable material including, but not limited to, flexible plastics such as silicone or polyurethane.

The shell 426 may also removably grip the sensor unit 422 to provide further maintenance of the attachment of the sensor unit to the base 424. In the illustrated embodiment, the shell 426 defines a receiving cavity 438 with sidewalls 440 around the cavity and a rim 442 around the sidewalls. In operation, the shell 426 receives a portion of the sensor unit 422, as illustrated in FIGS. 4B and 4C. In some embodiments, the sidewalls 440 or rim 442 may be resiliently flexible to expand when the portion of the sensor unit 422 is received in the cavity 438 and then compress against a perimeter of the received portion of the sensor unit 422. Preferably, at least the rim 442 or sidewalls 440 (or both) of the base 424 are made of a material that grips the sensor unit 422 by adhesion, compression, or the like or any combination thereof. In at least some embodiments, the sensor unit 422 may have a groove 490 that can receive the rim 442 to further facilitate maintaining the attachment of the sensor unit to the base 424. In at least some embodiments, the sidewalls 440 slope outwardly and downwardly from the rim 442 to form an undercut region below the rim. The sensor unit 422 can be similarly formed with a sloping housing to fit in the undercut below the rim 442 of the base 424 to further facilitate maintaining engagement between the sensor unit and the base. It will be recognized that in addition or as an alternative to the magnets (or magnet and magnetically attracted material) any other suitable type of mechanical fastener can be used to fasten the sensor unit 422 to the base 424.

The adhesive can be applied to the base 424 or can be an adhesive disposed on two sides of a substrate with one side of the substrate adhered to the base 424. Preferably, the adhesive is selected to be water resistant and resist losing adherence due to contact with sweat. In at least some embodiments, the base 424 or the adhesive on the base is intended for use for at least one, two, three, five, seven, or ten days or two, three, or four weeks or more under normal usage conditions before replacement or reapplication of adhesive. In at least some embodiments, the adhesive is selected to maintain adhesion to the skin when the user takes a shower. In at least some embodiments, the adhesive is selected to maintain adhesion to the skin when the user takes a bath, swims in a pool, or sits in jacuzzi, hot tub, or rehabilitation pool.

The base 424 optionally includes a tab 432 disposed at any suitable position relative to the shell 426. The tab 432 can facilitate removal of the sensor unit 422 from the base 424 by pushing or pulling on the tab 432 to deform the shell 426 to free the sensor unit. Preferably, operation of the tab 432 to disengage the sensor unit 422 can be performed while maintaining attachment of the base 424 to the skin of the patient. In some embodiments, operation of the tab 432 can also facilitate engagement of the sensor unit 422 with the base 424.

Figure 4E:
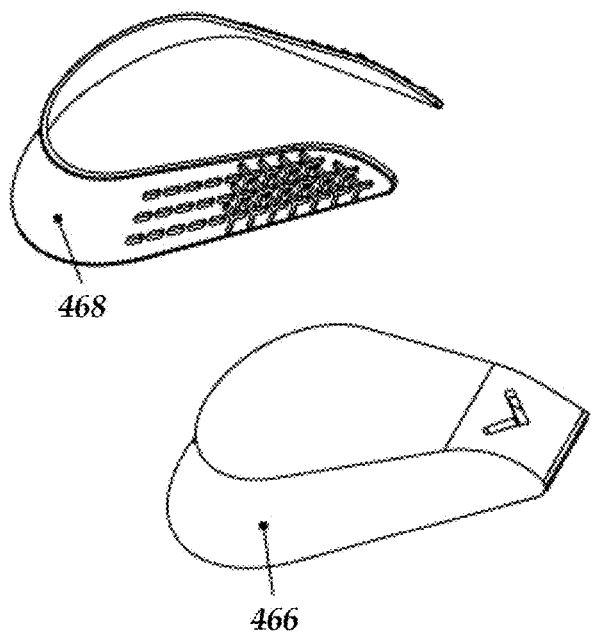
FIG. 4E is an exploded view of one embodiment of a housing of the sensor unit of FIG. 4A, according to the invention.

The illustrated sensor unit 422 includes an upper housing 450, a lower housing 452, a magnet 454, an electronics assembly 456, a power source 458, a light emission arrangement 460, and adhesive 462, 464, as illustrated in FIG. 4D. In addition, in some embodiments, as illustrated in FIG. 4E, the upper housing 450 can include a main housing 466 and a gripping element 468. In some embodiments, the sensor unit 422 can include more or fewer components than those illustrated in FIG. 4D.

The upper housing 450 and lower housing 452 form a cavity within which at least the electronics assembly 456 and power 458 source reside. The upper housing 450 and lower housing 452 can be made of any suitable material, such as metal or plastic materials (preferably, rigid plastic materials) or any combination thereof. In at least some embodiments, the upper housing 450 and lower housing 452, as well as the joining of the upper housing to the lower housing, are water resistant to resist ingress of water, sweat, rain, and other fluids into the interior of the housing. In at least some embodiments, the sensor unit 422 is sufficiently water resistant to allow the patient to shower without any covering over the sensor unit. In some embodiments, the sensor unit 422 is sufficiently water resistant to allow the patient to bathe or swim without any covering over the sensor unit.

The optional gripping element 468 can have a roughened or otherwise non-smooth surface on at least a portion of the gripping element. This non-smooth surface facilitates gripping of the sensor unit 422, particularly for engaging or disengaging the sensor unit from the base 424. In the illustrated embodiment, the gripping element 468 is a separate element that is overmolded, adhered, or otherwise attached to the main housing 466. The gripping element 468 may be made of a different, more flexible material than the main housing 466, such as silicone or polyurethane. In other embodiments, the gripping element 468 is formed as part of the main housing 466 by roughening or otherwise making at least a portion of the surface of the main housing non-smooth.

The magnet 454 is arranged for magnetically coupling to the magnet 428 of the base 424. In some embodiments, one of the magnets 454, 428 can be replaced with a magnetically attracted material that will then couple with the other magnet 454, 428 to magnetically coupled the base 424 to the sensor unit 422. In the illustrated embodiment, the magnet 454 is attached to the lower housing 452 by adhesive 464 which can be a layer of adhesive or adhesive disposed on both sides of a substrate. In other embodiments, the magnet 454 may be attached to the lower housing 452 by any other suitable method or may be disposed within the cavity formed by the upper housing 450 and lower housing 452.

The power source 458 can be any suitable power source. For example, the power source 458 can be a primary cell (e.g., a battery) and may have an expected lifetime, under normal usage, of at least 7, 10, 20, 40, 60, 90, 100, 70, or 180 days or more. In some embodiments, the primary cell may be replaceable. In some embodiments, the power source 458 is rechargeable using, for example, a recharge port or an inductive recharge device (such as an inductive mat or sleeve), or using WiFi or ultrasonic charging or any other suitable recharging method. In some embodiments, the primary cell (e.g., battery) can be the magnetically attractive material that the magnet 428 of the base 424 can be magnetically coupled to.

The electronics assembly 456 can contain any suitable components for operation of the sensor unit 422. In the illustrated embodiment, the electronics assembly 456 comprises a circuit board 468, a sensor processor 404, a temperature sensor 470, an accelerometer 472, at least one LED 474, a communications arrangement 476, and a magnetic switch 478. Adhesive 462 can couple the circuit board 468 to the lower housing 452. Other adhesive (not shown) may couple the circuit board or other components to the upper housing 450.

The sensor processor 404 can be similar to the sensor processor 104 described above and may have more or fewer capabilities than that sensor processor 104. In some embodiments, the sensor processor 404 may include analysis algorithms for analyzing or partially analyzing the sensor data. In other embodiments, the sensor processor 404 may be primarily designed to receive, store, and transmit sensor data.

The illustrated sensor unit 422 includes a temperature sensor 470 and an accelerometer 472, but other embodiments can contain more or different sensors, in any suitable combination, as described above. In the illustrated embodiment, the temperature sensor 470 is a thermistor which extends away from the circuit board 468 and through an opening 466 in the lower housing 452. When the sensor unit 422 engages the base 424, a portion of the temperature sensor 470 extends through the opening 430 in the base 424 so that the temperature sensor 470 is exposed to the skin of the patient and may be in contact with the skin of the patient.

The communications arrangement 476 operates with the sensor processor 404 to communicate with patient or clinician devices or other devices, as described above. Any suitable communications method or protocol can be used including, but not limited to WiFi, Bluetooth™, near field communications, infrared, radio frequency, acoustic, optical, or the like.

In some embodiments, the electronic assembly 456 also includes a magnetic switch 478, such as a reed switch, that is coupled to the sensor processor 404 so that when positioned near the magnet 428 of the base 424 is actuated to place the sensor unit 422 in an active mode. In at least some embodiments, when the sensor unit 422 is removed from the base 424 the magnetic switch is actuated to place the sensor in an inactive or standby mode. Alternatively or additionally, the sensor unit 422 may include a button, mechanical switch, or other mechanism to place the sensor into the active mode or into an inactive or standby mode or to toggle between modes or to turn the sensor unit on or off. Also, alternatively or additionally, the sensor unit 422 may be placed into the one of these modes (or toggled between modes) using signals from a patient or clinician device or other device communicating with the sensor unit 422. In at least some embodiments, in the inactive or standby mode, the sensor unit 422 continues to be receptive to signals from an external source (such as the patient or clinician device). In at least some embodiments, in the inactive or standby mode, the sensor unit 422 also maintains an internal clock.

The at least one LED 474 is coupled to the light emission arrangement 460 to provide light to the light emission arrangement. In at least some embodiments, the light emission arrangement 460 includes a light emitter 480 and a light pipe 482 to direct light from the LED(s) 474 to the light emitter. The light emission arrangement 460 provides an indication of operation of the device to a user or patient. For example, the light emission arrangement 460 may be lit when the sensor unit 422 is operating or is in the active mode. In some embodiments, the color of light emitted by the light emission arrangement may indicate which mode (active or inactive/standby) the sensor unit is currently in or may indicate operations being performed by the sensor unit (for example, transmitting, sensing, not sensing, synching with a patient or clinician device, or the like). In some embodiments, instead of, or in addition to, color, flashing of the light or brightness of the light may be used to indicate mode or operations. As an example, a flashing blue light may indicate synching with a patient or clinician device, a green light may indicate the active mode, and the absence of light may indicate the inactive/standby mode.

U.S. patent application Ser. Nos. 15/077,809 and 15/077,793 and U.S. Provisional Patent Applications Ser. Nos. 62/136,892 and 62/136,925, all of which are incorporated herein by reference, describe additional features and arrangements that can be incorporated in the wearable devices and sensor units described herein. These patent applications also describe other wearable or implantable devices that can be used in the methods and systems described herein.

In some embodiments, a second sensor unit can be used. For example, the second sensor unit can be placed on or within the same leg on the other side of the joint. As another example, a second sensor unit may be placed on the other leg for use in detecting or observing limp or other gait deficiencies or placed on the torso to detect or observe body orientation. A second sensor unit (or more additional sensor units) may also be used when two or more replacements are implanted in the body, for example, with multiple joint or vertebra replacements, to detect or observe, for example, subluxations, changes or defects in posture, scoliosis, or the like.

The two sensor units optionally can communicate or sync with each other. In at least some embodiments, the two sensor units can sync to each other and know where each one is in space and their location from each other in terms of distance and orientation. As an example, the two sensor units may triangulate their positions using a patient or clinician device. In at least some embodiments, if one of the sensor units is replaced or removed from its base, the patient device or other sensor unit is advised. When the sensor unit is reattached to its base or a new sensor unit is attached to the base, the system can determine the location or distance of the new sensor unit relative to the other sensor unit.

The sensors in the two sensor units can be used to measure flexion angles; range of motion; calculate vectors, angles, rays, planes or distances; and the like. Temperature sensors on the two sensor units can be used to determine temperature differences between two portions of the body. The sensors from the two sensor units can be used to calculate angles or other information that can be used to send signals to the patient if the patient is exceeding limitations on movement of range of movement during physical therapy or rehabilitation.

As indicated above, an implanted or wearable sensor unit, a sensor processor, or a sensor can communicate with a patient device or clinician device to provide sensor data or information derived from the sensor data. The sensor data can be used to determine range of motion measurements, exercise information, and the like. As an example, in some embodiments, the implanted or wearable sensor unit (or a combination of implanted or wearable sensor units) contains a temperature sensor and one or two accelerometers. These sensors can provide sensor data corresponding to skin temperature, number of steps (which might also be obtained from a patient device such as a smartphone), and x, y, and z positions of the accelerometers. Such sensor data may be used to determine a tilt angle of the sensor unit; range of motion measurements such as pivot point distance, temperature trends (for example, a 5 or 7 day temperature trend), range of motion angle, extension, flexion, or quadriceps or joint force; indications of notable events, such as fall; indication of limp or other gait abnormalities; exercise counts; or identification or classification of exercises; or the like or any combination thereof. Below are examples of methods for using sensor data for these and other purposes.

This systems and methods can allow the patient, clinician, physical therapist, or hospital or nursing personnel to passively and accurately monitor the patient's range of motion throughout the rehabilitation process. Utilizing machine learning tools to enhance the evaluation of the sensor data in accuracy over time providing better measurements with updates of the system using new training data sets. In at least some embodiments, the patient will not be required to notify the device when the exercise is being performed. The patient would only be required to wear the device. The methods described below can be applied in firmware, in software, in a patient device application, or on a server or any combination thereof.

Figure 5A:
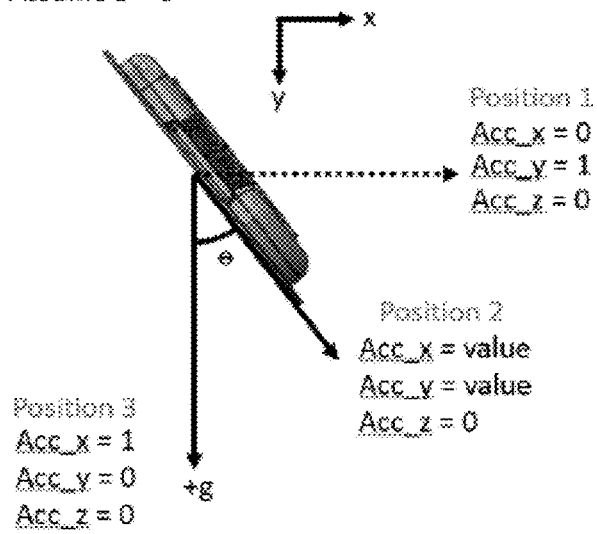
FIG. 5A is a diagram of one embodiment of a method for determining a tilt angle of a sensor unit, according to the invention.

FIG. 5A illustrates one method of determining a tilt angle of the sensor unit using a single accelerometer. The tilt angle determination assumes that at a tilt angle of 0 degrees (Position 1 in FIG. 5A) the accelerometer values for the x, y, and z positions are 0, 1, 0, respectively and that at a tilt angle of 90 degrees (Position 3 in FIG. 5A) the accelerometer values for the x, y, and z positions are 1, 0, 0, respectively. It will be understood by one of skill in the art that the x, y, and z positions of the accelerometer can be calibrated and normalize to provide these values. It will also be understood that the calculations described herein can be modified to account for other values of the x, y, and z positions of the accelerometer. In some embodiments, the system may request that the patient or clinician or other individual calibrate the accelerometer by positioning the sensor unit at 0 and 90 degrees or any two known angles. This may be performed before or after attaching the sensor unit to the patient. The readings of the accelerometer may also be normalized to give values of 1, as indicated above.

Under the conditions described above, the tilt angle, $\theta$ (in degrees) at any position (e.g., Position 2 in FIG. 5A), is equal to:

$$\theta = \frac{180}{\pi} \cos^{-1}(Acc\_y/rr)$$

$$rr = \sqrt{Acc\_x^2 + Acc\_y^2 + Acc\_y^2}$$

Where Acc_x, Acc_y, and Acc_z are the x, y, and z positions of the accelerometer that are normalized and calibrated as described above. Additionally, gyroscopic and accelerometer readings can be integrated to increase accuracy of the reading. Gyros respond quickly, but drift over time. Accelerometers respond slowly, but are accurate over time. A Kalman filter or complimentary filter can be applied to the data set to enhance accuracy and response time.

Using the tilt angle, a number of range of motion measurements can be determined. Figure B is one example of a diagram for determining tilt angle where line 590 represents the patient's femur and lines 592a, 592b represent the patient's tibia at first and second positions, respectively. The illustrated positions can correspond to the patient performing a sitting lift exercise. The femur angle, $\phi$, can be determined using the patient device 106 (FIG. 1—for example, a smart phone) that is rested on the patient's thigh and measures the angle of the patient device 106 (using, for example, a gyroscope or accelerometer or the like in the patient device). Angles $\psi_1$ and $\psi_2$ correspond to angles of the patient's femur at two extreme positions during the sitting lift exercise. The range of motion measurements of flexion, extension, and range of motion can be determined from these angles. Extension is equal to $\psi_1 - \phi$. Flexion is equal to $\psi_2 - \phi$. Range of motion ("ROM") is equal to $\psi_2 - \psi_1$.

FIG. 5C is a flow chart of one method of determining extension or flexion of the knee using the sensor unit. In step 511, the tilt angle of the patient device is determined. For example, the patient device may include a tilt angle sensor that can be used to determine the tilt angle of the patient device as it rests on the thigh of the patient. In some embodiments, a tilt angle of the patient device may instead have an assumed value based on data from a population of patients or an estimate of the tilt angle or the tilt angle of the device may be ignored in the subsequent steps or assumed to be zero degrees or other value. In step 513, the tilt angle of the sensor unit is determined. In some embodiments, the tilt angle of the sensor unit is determined by the processor of the sensor unit and then communicated to the patient device. In other embodiments, the sensor unit communicates the sensor data to the patient device which then determines the tilt angle of the sensor unit from the sensor data using the processor of the patient device. Alternatively, a portion of the determination may be performed by the processor of the sensor unit and another portion may be performed by the processor of the patient device.

In step 515, the extension or flexion of the knee can be determined using the tilt angles of the patient device and sensor unit. The maximum extension can be determined with the leg of the patient at the maximum backward extension and the maximum flexion can be determined with the leg of the patient at the maximum forward extension.

Other range of motion measurements can be made in a similar manner with one or more sensor units disposed on respective portions of the body. For example, measurements of backward extension, forward flexion, left flexion, and right flexion of the back can be determined. With respect to the neck, extension, flexion, lateral bending to the left and right, and left and right rotation can be determined. With respect to the hip, backward extension, left and right flexion (with the knee flexed or extended), left and right adduction, and left and right abduction can be determined. With respect to the shoulder, flexion, extension, adduction, and abduction can be determined. With respect to the elbow, flexion, extension, pronation, and supination can be determined. With respect to the ankle, flexion, extension, inversion, and eversion can be determined. With respect to the wrist, extension and flexion can be determined. With respect to the joints of the thumb or fingers, flexion can be determined. It will be recognized that other range of motion measurements can be made on those joints and other portions of the body. The method illustrated in FIG. 5C can be adapted to determine any of these range of motion measurements.

Figure 5B:
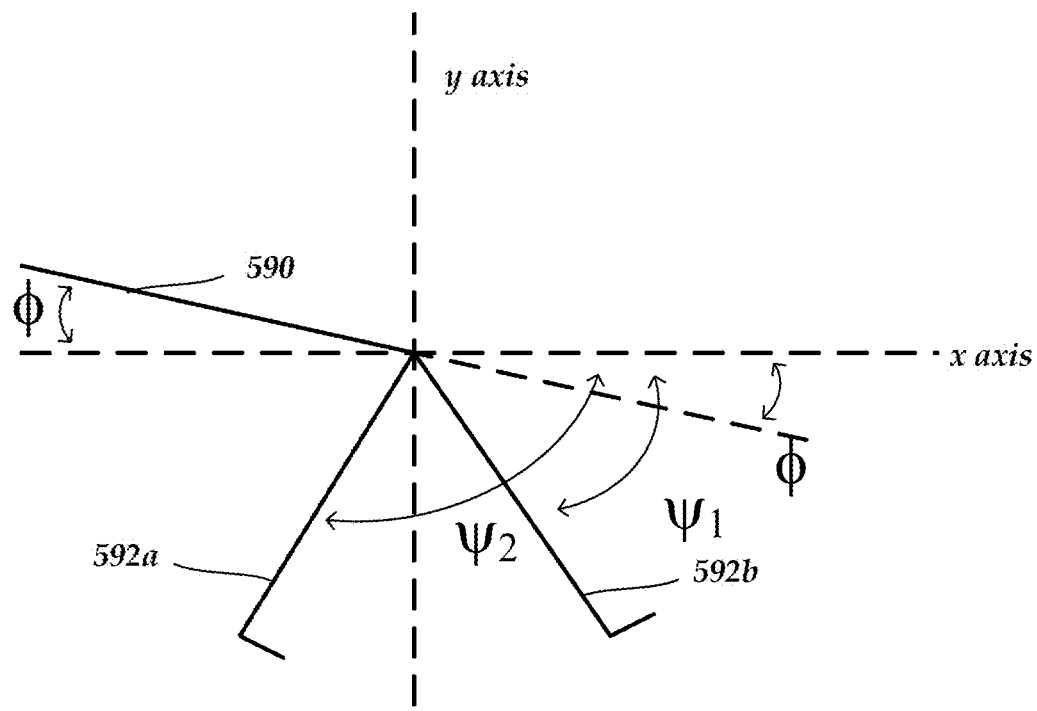
FIG. 5B is a diagram of one embodiment of a method for determining extension and flexion, according to the invention.
Figure 6A:
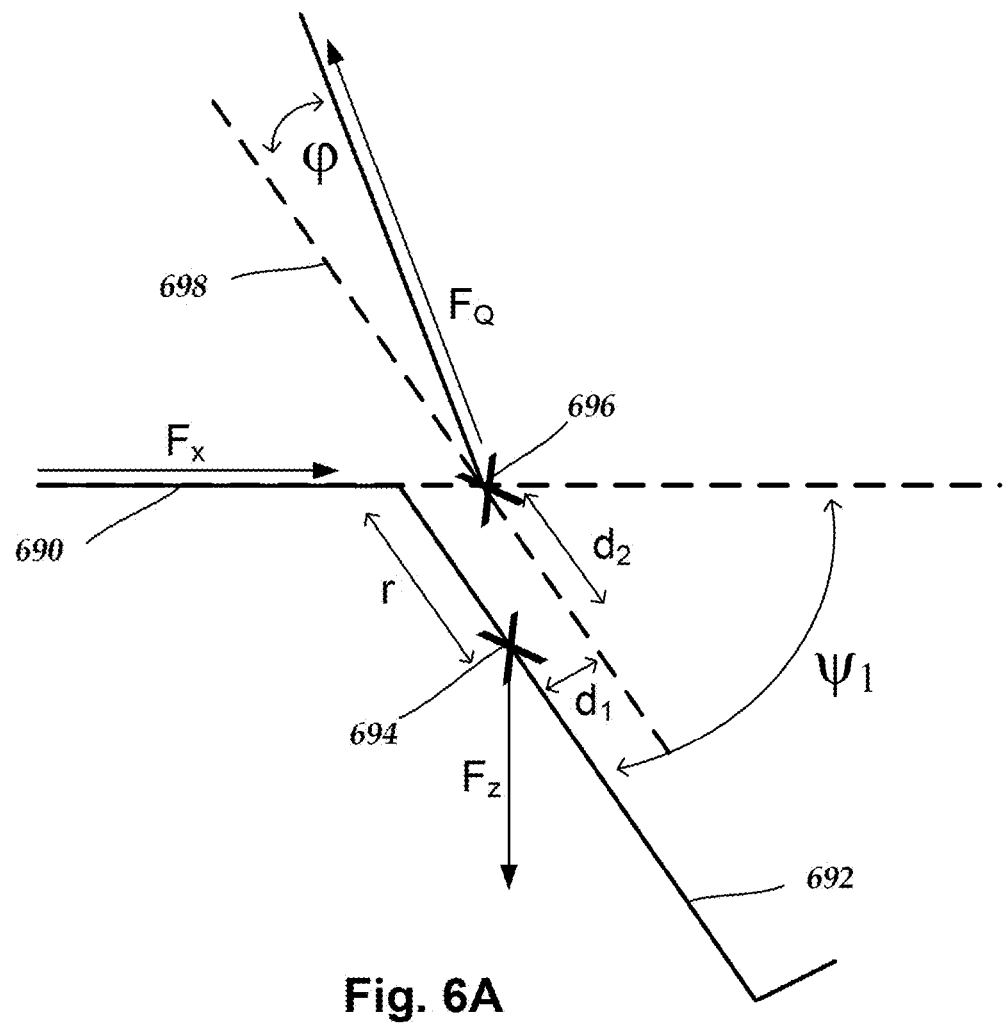
FIG. 6A is a diagram of one embodiment of a method for determining quadricep force, according to the invention.

Another range of motion measurement that can be estimated for the sitting lift is the quadriceps force. FIG. 6A is one example of a diagram for calculating the quadriceps force. In this drawing, the femur angle is assumed to be zero, line 690 corresponds to the femur, line 692 corresponds to the tibia, point 694 corresponds to the center of mass of the tibia, point 696 corresponds to the position of the tendon of the joint, and line 698 corresponds to the tendon line of action. The tendon has a line of action at an angle, $\varphi$, with respect to the tibia. For purposes of this calculation, the force, $F_x$, in line with the femur is assumed to equal 0 in the sitting lift. (It will be recognized by those of skill in the art that a non-zero $F_x$ can be easily incorporated in the calculation.) The force, $F_y$, due to the mass of the leg is given by $F_y$=mg, where m is the mass of the tibial leg segment and the foot and the g is the acceleration due to gravity. The torque for rotating the tibial leg segment is then: T=mgr cos($\psi_1$) where r is the distance from the joint center to the center of mass and $\psi_1$ is defined as the angle of the tibia to the horizontal (see, FIG. 5B). The torque can also be described relative to the quadriceps force, $F_Q$, as T=$F_Q d_1$ sin($\varphi$)+$F_Q d_2$ cos($\varphi$) where $d_1$ is the perpendicular distance between the tibia and the tendon line of action and $d_2$ is the parallel distance between the center of mass of the tibia and the position of the tendon on the joint, as illustrated in FIG. 6A.

This results in:

$$F_Q d_1 \sin \varphi + F_Q d_2 \cos \varphi = mgr \cos \psi_1,$$

yielding an estimate of the quadriceps force as $$F_Q = \frac{mgr\cos\psi_1}{d_1 \sin\varphi + d_2 \cos\varphi}$$

The values for m, $d_1$, $d_2$, and $\varphi$ can be measured or otherwise determined for the patient, can be estimated by the clinician or based on factors such as height and weight of the patient, or can be selected from average values for a population of patients or by any other method. The angle $\psi_1$ can be determined as described above or by another other suitable method.

FIG. 6B is a flow chart of one method of determining quadricep force using the sensor unit. In step 621, anatomical values such as m, $d_1$, $d_2$, and $\varphi$ are determined. Any of the methods described above can be used to determine these values. In step 623, the tilt angle of the sensor unit is determined. In some embodiments, the tilt angle of the sensor unit is determined by the processor of the sensor unit and then communicated to the patient device. In other embodiments, the sensor unit communicates the sensor data to the patient device which then determines the tilt angle of the sensor unit from the sensor data using the processor of the patient device. Alternatively, a portion of the determination may be performed by the processor of the sensor unit and another portion may be performed by the processor of the patient device. In step 625, the quadricep force can be determined using the tilt angle of the patient device and anatomic values, as described above.

Figure 7:
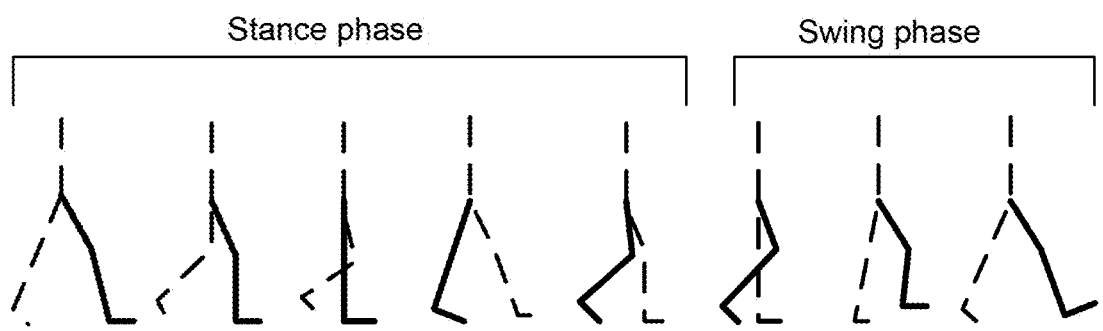
FIG. 7 is a diagram for analyzing gait, according to the invention.

FIG. 7 illustrates a normal gait of a person with the leg nearest the viewer of FIG. 7 being a solid line and the leg furthest from the viewer being a dotted line. The sensor unit can be utilized to characterize and evaluate a patient's gait by, for example, monitoring the tilt angle or the movement and tilting of the sensor unit through space. In at least some embodiments, the sensor data from the sensor unit can be utilized to detect limping. For example, a limp can be identified when the tilt angle does not pass through the back of the leg indicating that the swing phase (FIG. 7) of the gait is not completed fully.

In some embodiments, the sensor data may be useful for detecting notable events, such as falls. These events may be recognized from the sensor data as shocks to the data or rapid, unexplained changes in tilt angle or other measurements determined from the data. In some embodiments, the patient device may execute a warning or alert or may request confirmation from the patient that the patient has fallen. In some embodiments, the sensor unit or patient device may send a warning or alert to the clinician device when a notable event, such as a fall is detected or if multiple notable events (at least two, three, four or more) occur within a short period of time (for example, within 10 minutes, 30 minutes, one hour, two hours, or more).

Figure 8A:
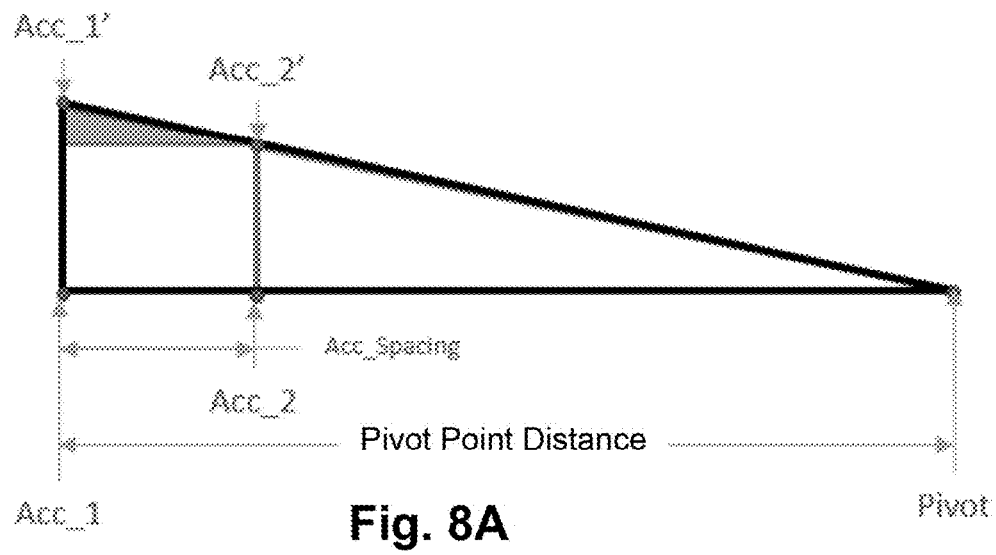
FIG. 8A is a diagram of one embodiment of a method for determining a pivot point distance, according to the invention.

In at least some embodiments, the sensor data can be used to identify or classify the type of exercise a patient is doing and to count the number of repetitions. FIG. 8A illustrates one measurement that can be derived from the sensor data to assist in identifying or classifying an exercise. In this embodiment, the sensor unit contains two accelerometers or two sensor units, with one accelerometer each, are positioned on the patient. In addition, the distance between the two accelerometers is known or at least constant. Many, if not all, of the exercises have a pivot point associated with the exercise. For the heel slide, the pivot point is the ankle; for the straight leg raise, the pivot point is the hip; for the sitting lift, the pivot point is the hip, and for the knee to chest exercise, there is no pivot point.

Figure 8B:
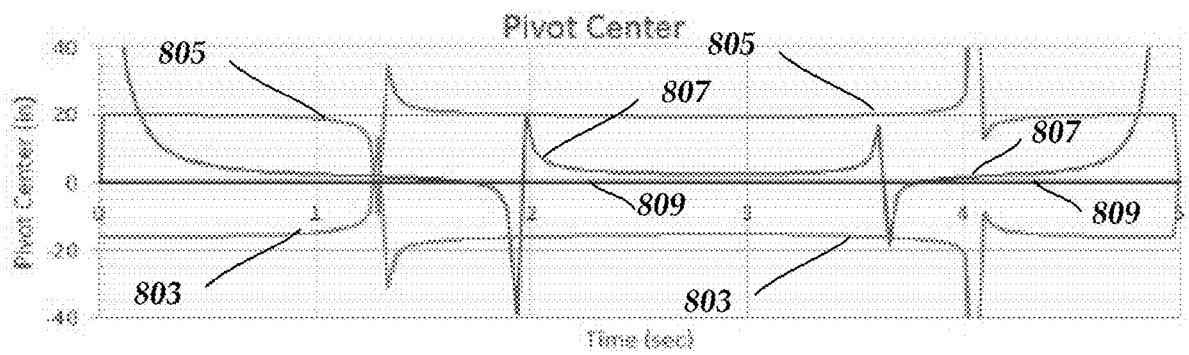
FIG. 8B is a graph of pivot point distance over time for four different exercise, according to the invention.
Figure 8C:
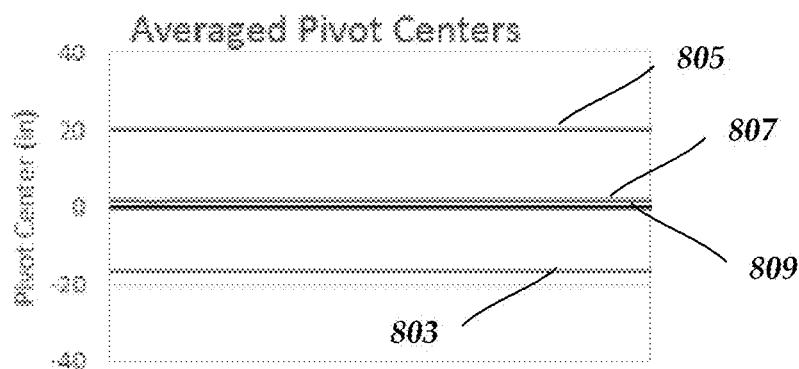
FIG. 8C is a graph of average pivot point distance for four different exercise, according to the invention.

As illustrated in FIG. 8A, the pivot point distance (i.e., the distance from the pivot point to the first accelerometer) can be determined (using similar triangles) as Pivot point distance=$Acc_{spacing}*Acc'_1/(Acc'_1-Acc'_2)$ where $Acc_{spacing}$ is the distance between the two accelerometers at a first position, $Acc'_1$ is the position of the first accelerometer at a second position, and $Acc'_2$ is the position of the second accelerometer at the second position. In some embodiments, the distances can be three-dimensional distances. In other embodiments, the distances may be two-dimensional distances taken in a plane. FIG. 8B illustrates a measurement of pivot point distance over time for heel slide 803, sitting lift 805, straight leg raise 807, and knee to chest 809 and FIG. 8C is an average pivot point distance for these exercises. In the illustrated embodiments, the average pivot point distance for the exercises are as follows: heel slide −15 in (about −38 cm); sitting lift 2 in (about 5 cm); straight leg raise 19 in (about 48 cm); and knee to chest 0 in (0 cm).

Thus, each of these exercises has a different value for average pivot point distance. In some embodiments, the average pivot point distance for each exercise can be determined by having the patient perform the exercise while determining the average pivot point distance. In some embodiments, the average pivot point distance for each exercise may be selected from a database of all or a subset of patients or may be estimated for the patient based on height or length/distance measurements (e.g., length of tibial portion of leg and length of femur portion of the leg or distance from sensor unit to ankle, hip, knee, or the like).

The average pivot point distance can then be determined as the patient exercises and can be compared to previously established values for each exercise to determine which exercise the patient is currently performing. In this manner, the patient is not required to identify which exercise is being performed on the patient device. The number of repetitions of an exercise may be determined by noting excursions in the pivot point distance determinations or by patterns or the like in the tilt angle determined from the sensor unit or the like or any other suitable method.

FIG. 8D is a flow chart of one method of identifying or classifying an exercise based on sensor data. In step 811, a pivot point distance is determined, as described above, during an exercise. In some embodiments, an average pivot point distance may be determined over a period of time instead of at a single point in time. In step 813, the determined pivot point distance is compared with pre-determined average pivot point distances for a number of different exercises. The pre-determined average pivot point distances can be obtained by any suitable method including those described above. In some embodiments, the identification or classification is based simply on comparison. In some embodiments, algorithms such as K-Nearest Neighbor Learning Vector Quantization can be used to facilitate the identification or classification. In step 815, the current exercise is identified or classified based on the comparison, as described above.

The pre-determined average pivot points for exercises can be provided to the system from previous calculations for the patient or from a database of values for a particular patient population or from any other suitable source. It may be desirable to improve those pre-determined average pivot points. FIG. 8E illustrates one method of improving the classification of exercises. In step 821, anatomical information is input. This anatomical information may be, for example, the height of the patient or, more measurements may be input such as measured distances from the knee to the ankle or hip. In step 823, pivot point distances are then predicted, based on the input anatomical information, for multiple exercises. In some embodiments, step 821 is skipped the pivot point distances are estimated by the clinician or from averages for a particular population of patients (e.g., averages for adult males or adult females or the like). In step 825, the patient preforms an exercise and the system determines the pivot point distance. Using the determined pivot point distance, the system identifies or classifies the exercise that is being performed. In some embodiments, the identification or classification is based simply on comparison. In some embodiments, algorithms such as K-Nearest Neighbor Learning Vector Quantization can be used to facilitate the identification or classification. In step 827, the user identifies the exercise being performed and compares that with the identification or classification made by the system. In step 829, he results can be used to modify the initial pivot point distances associated with the exercises to refine the predictions. Steps 825-829 can be performed repeatedly for each exercise and for different exercises to refine the pivot point distance for each exercise.

In some embodiments, the determination of a pivot point may facilitate identification of the position of the sensor unit relative to a wound. This may be useful for assessing accuracy of temperature readings or for providing feedback to the patient regarding better placement of the sensor unit. In addition, the determination of the pivot point may facilitate understanding of the patient anatomy by, for example, providing estimates of the length of the femur or tibia using pivot point measurements related to the ankle, knee, or hip. In some embodiments, more accurate femur or tibia lengths can improve analysis of gate, stride length, limp detection, or fall detection/classification.

FIGS. 9-12 illustrate screenshots of one embodiment of an application or user interface for the patient device or clinician device. Additional description of the application or user interface, as well as other embodiments of applications and user interfaces, can be found at U.S. patent application Ser. Nos. 15/077,809 and 15/077,793 and U.S. Provisional Patent Applications Ser. Nos. 62/136,892 and 62/136,925, all of which are incorporated herein by reference, as well as U.S. patent application Ser. No. 15/422,312, entitled "Systems and Methods using a Wearable Device for Monitoring an Orthopedic Implant and Rehabilitation", and U.S. patent application Ser. No. 15/422,320, entitled "Systems and Methods with User Interfaces for Monitoring Physical Therapy and Rehabilitation", both of which are filed on even date herewith and incorporated herein by reference. The illustrated user application interface is particularly useful for a mobile device such as a smartphone or tablet, but can also be used with other devices such as desktop or laptop computers.

Figure 9:
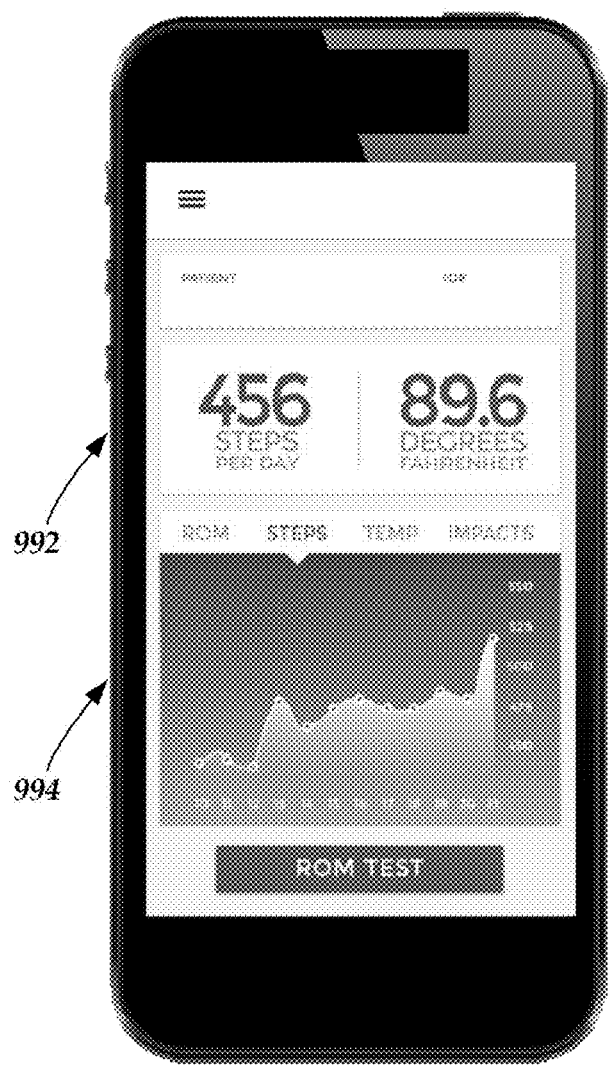
FIG. 9 is a diagram of one embodiment of a user interface for a mobile device to display information obtained from a sensor unit, according to the invention.

FIG. 9 illustrates another page of the user interface or application that provides information such as steps per day (or number of repetitions of an exercise or the like) and a temperature measurement as shown in section 992. The user interface 990 may also include a section 994 that shows graphs of the data such as the hourly number of steps, as illustrated in FIG. 9. The illustrated user interface permits the user to select from other charts such as exercise history (labeled "ROM"), temperature or temperature trends, and number of impacts or shocks to the sensor module. It will be understood that other measurement or observations from the sensor described above can be graphed. In at least some embodiments, the user may also be able to select the time period of the graph to display data in periods of time such as, for example, minutes, hours, days, or weeks.

This user interface can be useful in monitoring patient activity and progress. The graphs in section 994 may be useful for showing patient exercise history and progress. In some embodiments, the user interface may also allow the user to set goals such as, for example, a number of steps or a number of exercise repetitions over a particular period (for example, 1, 2, 4, 6, or 7 hours or 1 day or 1 week). The user interface may also display the current status towards attaining those goals. The user interface may also highlight notable events, such as, for example, the largest number of steps or exercise repetitions, elevated temperature readings, large numbers of impacts or shocks, or the like. The user interface may also highlight the attainment of goals.

Figure 10:
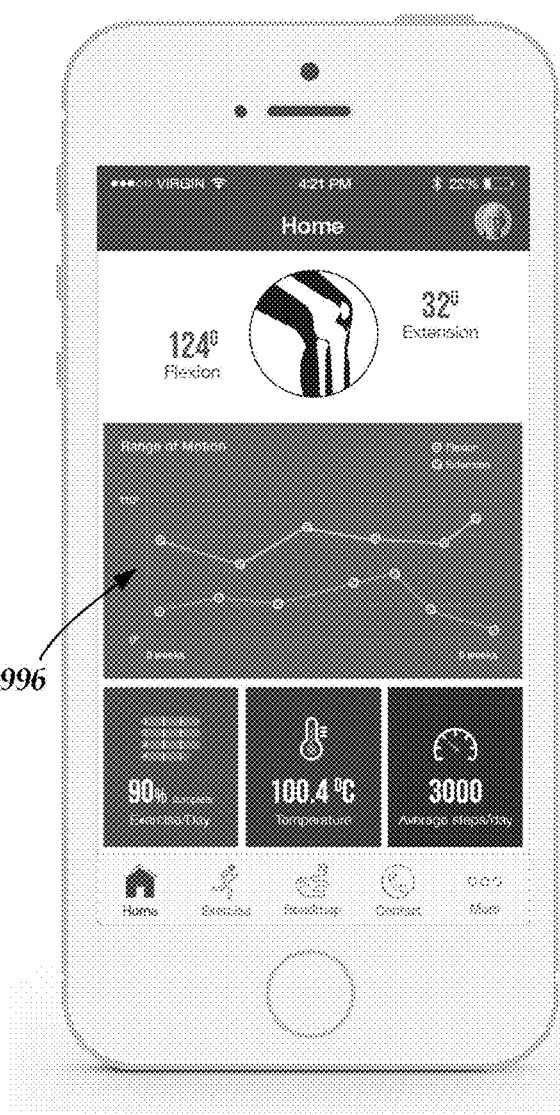
FIG. 10 is a diagram of one embodiment of a user interface for a mobile device to display a range of motion measurement, according to the invention.

FIG. 10 illustrates another page of the user interface or application that displays information related to particular patient measurements that can be tracked to monitor rehabilitation or physical therapy. In the illustrated page, the patient measurements are flexion and extension related to a patient's knee. These patient measurements can include, but are not limited to, range of motion measurements such as flexion and extension. The page also illustrates a chart 996 tracking the progress of these measurements. The progress may be tracked hourly, daily, weekly, or over any other period of time. In some embodiments, the user interface or application allows the user to select or change the time period illustrated in the chart. The page in FIG. 7 also provides information about other measurements such as percentage of exercise completion, skin temperature, number of steps or the like.

Figure 11:
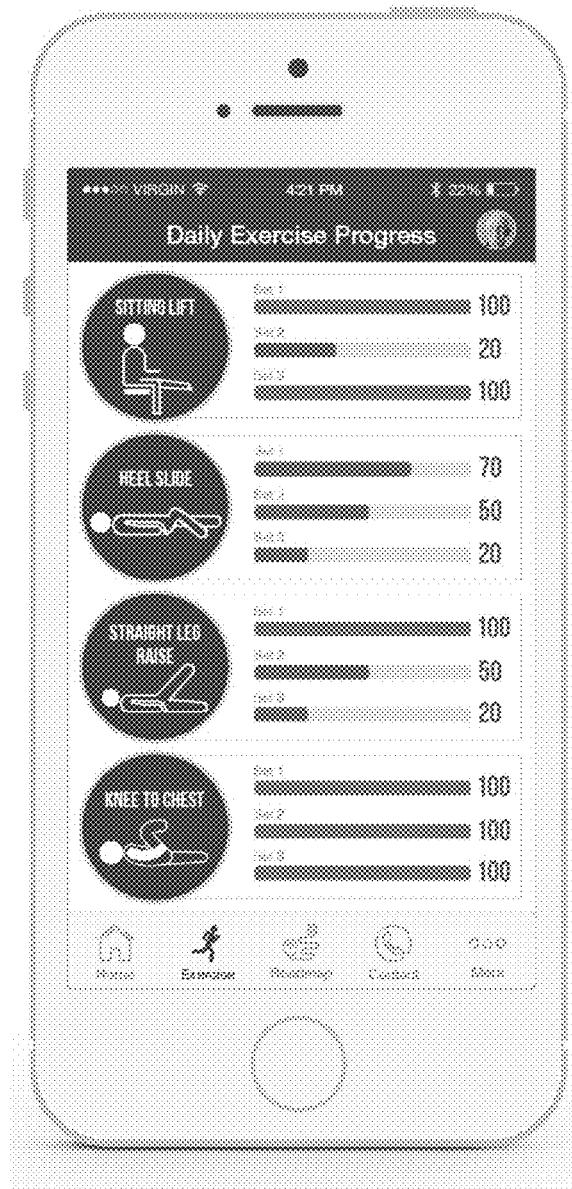
FIG. 11 is a diagram of one embodiment of a user interface for a mobile device to display a summary of repetitions of exercises, according to the invention.

FIG. 11 illustrates another page in which the user interface or application tracks the daily exercise program. In the illustrated embodiment, the exercises are sitting lift, heel slide (hip and knee flexion), straight leg raise, and knee to chest. Other exercises can include, but are not limited to, standing lift, ankle pump, ankle circle, thigh squeeze (quadriceps set), lying kick (short arc quadriceps), knee bend (sitting knee flexion), prolonged knee stretch, sitting kick (long arc quadriceps), keen straightening stretch, knee dangling/swinging, hamstring set (heel dig), buttocks squeeze (gluteal set), walking, or the like. These exercises are directed to knee rehabilitation. Of course, rehabilitation or physical therapy for other joints or body regions can include a different set of exercises. In addition, the page illustrates the percentage of completion for each set of repetitions (in this case, three sets) that are to be performed by the patient.

Figure 12:
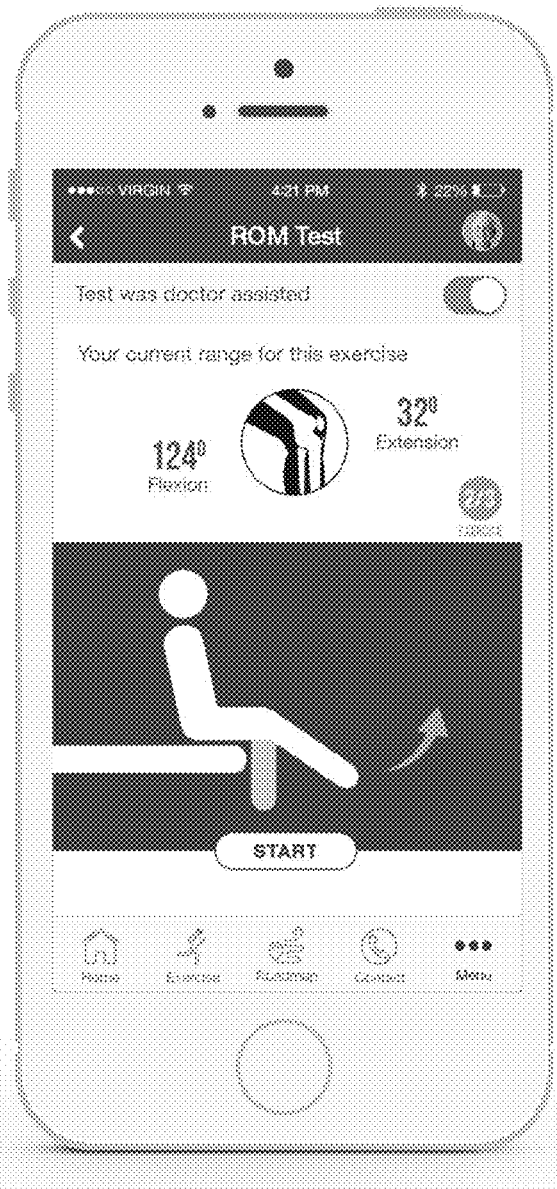
FIG. 12 is a diagram of one embodiment of a user interface for a mobile device to display information obtained from a sensor unit, according to the invention.

FIG. 12 illustrates yet another page with a single exercise. This page illustrates the current measurements associated with the exercise (in this case, flexion and extension). The page also illustrates how the exercise is performed and may include a control for the patient to indicate that the exercise is to be begun. In some embodiments, the page may also provide an indication of the number of repetitions (or the number of repetitions that are still needed to achieve a repetition goal) as the patient exercises. The page may also indicate patient measurements based on the exercise (e.g., a current measurement for the latest repetition or an average measurement for the current set of repetitions or a maximum measurement for a set of repetitions) and may also indicate a goal for the measurement. This page may include a meter with bars or the like to indicate what portion of an exercise goal has been met. An indication (such as a bar or the like) may also indicate what portion of a range of motion or other therapy goal has been met. In some embodiments, the page may display an average patient time to the range of motion goal or the like to motivate the patient.

Figure 13:
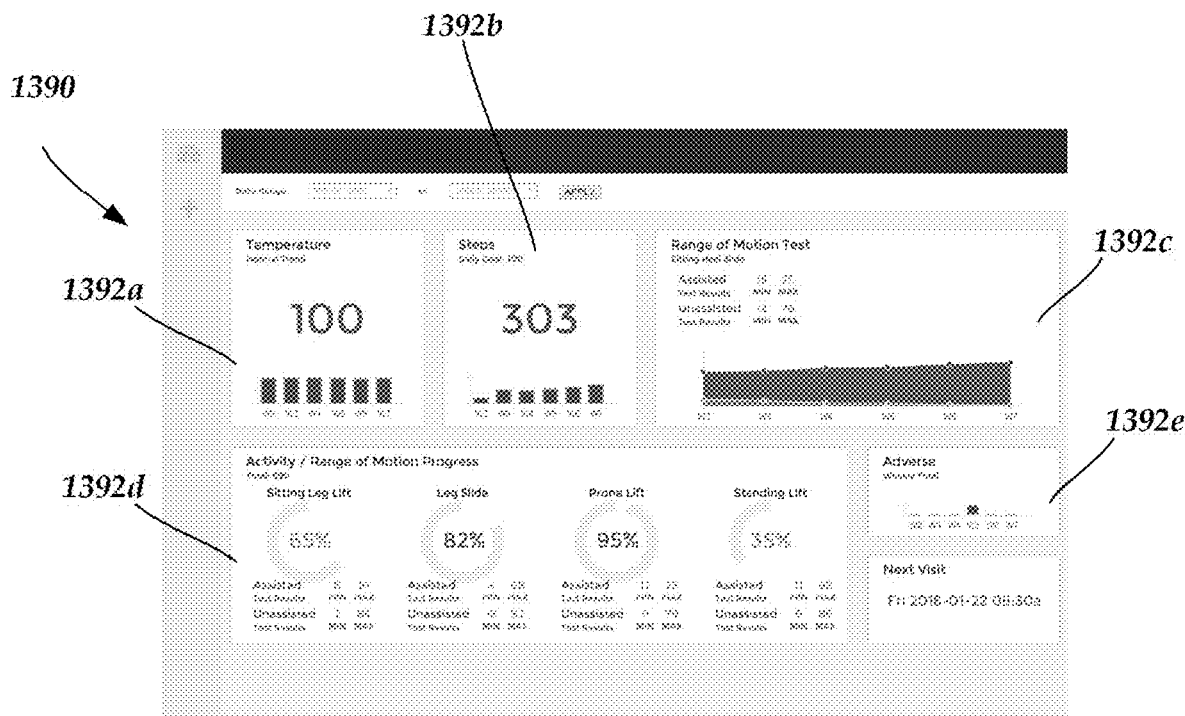
FIG. 13 is a diagram of another embodiment of a user interface to display information obtained from a sensor unit, according to the invention.

FIG. 13 illustrates a user interface 1390 that may be suitable for a computer or web interface. The illustrated user interface includes a region 1392 displaying the results of temperature measurements 1392a, step measurements 1392b, range of motion tests 1392c, specific exercises and tests 1392d, and adverse events 1392e. These results may include numerical information and graphical information. These results may also illustrate graphically or numerically the degree of success in performing exercises (see, for example, region 1392d) and may also illustrate the degree of compliance with rehabilitation activities (such as the number of exercise repetitions performed). Such an arrangement of information can facilitate monitoring or patient progress, identification of progress or lack of progress, identification of concerns (such as elevated temperature or elevated number of shocks or impacts), and the like.

Other information that can be displayed in one or more pages on the user interface can be include any suitable patient rehabilitation progress data include baselines and progress over time. For example, the information can include baseline range of motion information for exercises such as a sitting leg lift, heel slide, standing lift, prone lift, or the like. The information may also include current range of motion information for these exercises. The information may also include step analysis information including, but not limited to, pre-operation and post-operation average cadence, maximum cadence, stride angle, as well as time spent walking, biking, running, or in sedentary activities. Additional information can include skin temperature, ambient temperature, and trends in temperature. The user interface may also provide information about how many times or how often the patient falls or other notable events. The user interface may provide information from GPS readings from the wearable device or patient device to assess baseline activity, current activity, general activity after surgery or physical therapy or the like.

The user interface of a clinician device may also be used to conduct in-office range of motion tests. The clinician device or patient device may be used to create video of range of motion exercises.

Figure 14:
FIG. 14 is a diagram of a further embodiment of a user interface to display information obtained from a sensor unit, according to the invention.

FIG. 14 illustrates a user interface 1490 for a clinician to monitor multiple patients. The region 1492 includes information such as patient name, surgery date, sensor date and results of tests 1492a, number of adverse events, location of the orthopedic implant, and the like. The clinician may also track number of surgeries 1494, rate of successful rehabilitation 1496, and other suitable information such as, for example, total number of surgeries (for example, total number of knee replacements), average time to reach a particular rehabilitation outcome (for example, average time to reach specified range of motion), and the like.

Figure 15:
FIG. 15 is a diagram of yet another embodiment of a user interface to display information obtained from a sensor unit, according to the invention.

FIG. 15 illustrates another user interface for a clinician to monitor patients. The region 1592 includes information such as patient name, gender, surgery date, days post operation, measured or trending temperature, range of motion measure, activity, number of steps, notable events, implant site, wearable device status, and the like. The clinician may also track number of successful rehabilitations 1594, range of motion achieved over time for a group of patients 1596, and other suitable information. Controls may also be provided to access individual patient records 1598 or access patient alerts 1599.

In at least some embodiments, the applications or user interfaces described herein can be web or application interfaces that are accessible when the patient device or clinician device accesses a server for a content provider. In at least some embodiments, the server or other servers or memory storage devices can store information for the web interface and may also store patient-specific information including patient identification data, sensor data or information derived from sensor data, patient or clinician comments or the like, or any other suitable data. In at least some embodiments, the patient-specific information can be accessed from the patient device, clinician device or other device which, in some embodiments, may require providing credentials (e.g., username or password or both) to access the information.

Additional user interfaces and methods of calculating or otherwise determining information relating to the physical therapy, rehabilitation, or status of the patient are described in U.S. patent application Ser. No. 15/422,312, entitled "Systems and Methods using a Wearable Device for Monitoring an Orthopedic Implant and Rehabilitation", and U.S. patent application Ser. No. 15/422,320, entitled "Systems and Methods with User Interfaces for Monitoring Physical Therapy and Rehabilitation", both of which are filed on even date herewith and incorporated herein by reference.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A system for monitoring a patient, the system comprising:
    a sensor unit configured and arranged to be disposed on or within the patient, the sensor unit comprising a first housing, an accelerometer disposed in the first housing, and a wireless communication arrangement disposed in the first housing; and
    a patient device configured and arranged for communication with the sensor unit, the patient device comprising a second housing, a display on the second housing, a tilt angle sensor disposed in the second housing, a memory disposed in the second housing, and a processor disposed in the second housing and coupled to the display and memory, wherein the processor is configured and arranged for performing actions comprising:
        determining a tilt angle of the patient device, when the patient device is sitting on a thigh of the patient, using the tilt angle sensor of the patient device;
        obtaining a tilt angle of the sensor unit disposed on a portion of a leg of the patient below a knee of the patient; and
        determining an extension or flexion of the knee of the patient using the tilt angle of the patient device and the tilt angle of the sensor unit.

2. The system of claim 1, wherein determining the extension or flexion comprises determining a maximum flexion of the knee using the tilt angle of the sensor unit at a maximum forward extension of the knee.

3. The system of claim 1, wherein determining the extension or flexion comprises determining a maximum extension of the knee using the tilt angle of the sensor unit at a maximum backward extension of the knee.

4. The system of claim 1, wherein the actions further comprise determining an estimated quadricep force using the tilt angle of the sensor unit.

5. The system of claim 1, further comprising a base configured to receive the sensor unit, the base comprising a shell and adhesive disposed on a bottom surface of the shell, wherein the shell is configured to removably grip the sensor unit when the sensor unit is inserted into the shell.

6. The system of claim 5, wherein the sensor unit is configured to actuate into an active mode when inserted into the shell and to actuate into an inactive or standby mode when removed from the shell.

7. A system for monitoring a patient, the system comprising:
    at least one sensor unit configured and arranged to be disposed on or within the patient, the at least one sensor unit, in combination, comprising at least two accelerometers and a communication arrangement; and
    a patient device configured and arranged for communication with the at least one sensor unit, the patient device comprising a display, a memory, and a processor coupled to the display and memory, wherein the processor is configured and arranged for performing actions comprising:
        during performance of an exercise, obtaining a pivot point distance using the at least two accelerometers of the at least one sensor unit;
        comparing the obtained pivot point distance with pre-determined pivot point distances for a plurality of exercises; and
        based on the comparison, identifying the exercise being performed as a one of the plurality of exercises.

8. The system of claim 7, wherein obtaining the pivot point distance comprises obtaining the pivot point distance that has been determined by the processor of at least one of the at least one sensor unit.

9. The system of claim 7, wherein obtaining the pivot point distance comprises obtaining at least one position value from each of two of the accelerometers and calculating the pivot point distance from the obtained position values.

10. The system of claim 7, wherein obtaining a pivot point distance comprises obtaining an average pivot point distance over a period of time.

11. The system of claim 7, wherein the pre-determined pivot point distances for the plurality of exercises are average pivot point distances for the plurality of exercises for a population of patients.

12. The system of claim 7, wherein the pre-determined pivot point distances for the plurality of exercises are determined from one or more anatomical measurements of the patient.

13. The system of claim 7, wherein the actions further comprising determining a number of repetitions of the exercise being performed.

14. A system for monitoring a patient, the system comprising:
    at least one sensor unit configured and arranged to be disposed on or within the patient, the at least one sensor unit, in combination, comprising at least two accelerometers and a communication arrangement; and
    a patient device configured and arranged for communication with the at least one sensor unit, the patient device comprising a display, a memory, and a processor coupled to the display and memory, wherein the processor is configured and arranged for performing actions comprising:
- a) predicting average pivot point distances for a plurality of exercises;
- b) during performance of a one of the exercises, obtaining a pivot point distance using the at least two accelerometers of the at least one sensor unit;
- c) using the predicted average pivot point distances, identifying the exercise being performed; and
- d) refining the predicted average pivot point distance for the exercise being performed with the obtained pivot point distance.

15. The system of claim 14, wherein the actions further comprise repeating steps b)-d) for the one of the exercises, using the refined predicted average pivot point distance instead of the predicted average pivot point distance.

16. The system of claim 14, wherein the actions further comprise repeating steps b)-d) for an additional one or more of the exercises.

17. The system of claim 14, wherein obtaining the pivot point distance comprises obtaining the pivot point distance that has been determined by the processor of at least one of the at least one sensor unit.

18. The system of claim 14, wherein obtaining the pivot point distance comprises obtaining at least one position value from each of two of the accelerometers and calculating the pivot point distance from the obtained position values.

19. The system of claim 14, wherein the actions further comprise obtaining anatomical information for the patient, wherein predicting average pivot point distances for a plurality of exercises comprises predicting the average pivot point distances for the plurality of exercises using the anatomical information.

20. The system of claim 19, wherein the anatomical information comprises a height of the patient.

* * * * *